US009267116B2

(12) United States Patent
Kanamaru et al.

(10) Patent No.: US 9,267,116 B2
(45) Date of Patent: Feb. 23, 2016

(54) AMINO ACID DEHYDROGENASE, AND PROCESS FOR PRODUCING L-AMINO ACID, 2-OXO ACID OR D-AMINO ACID

(75) Inventors: Hiroyuki Kanamaru, Hyogo (JP); Ryuuji Miki, Hyogo (JP); Makoto Ueda, Hyogo (JP); Hironori Nanba, Hyogo (JP); Yoshihiko Yasohara, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 605 days.

(21) Appl. No.: 13/133,444

(22) PCT Filed: Dec. 8, 2009

(86) PCT No.: PCT/JP2009/006679
§ 371 (c)(1),
(2), (4) Date: Aug. 2, 2011

(87) PCT Pub. No.: WO2010/067578
PCT Pub. Date: Jun. 17, 2010

(65) Prior Publication Data
US 2011/0281309 A1 Nov. 17, 2011

(30) Foreign Application Priority Data

Dec. 9, 2008 (JP) ................................ 2008-313326

(51) Int. Cl.
| C12N 9/06 | (2006.01) |
| C12N 1/21 | (2006.01) |
| C12P 13/04 | (2006.01) |
| C07H 21/04 | (2006.01) |
| C12P 7/40 | (2006.01) |
| C12P 13/22 | (2006.01) |
| C12P 41/00 | (2006.01) |
| C12N 15/70 | (2006.01) |
| C12N 15/74 | (2006.01) |

(52) U.S. Cl.
CPC ............ *C12N 9/0016* (2013.01); *C12N 9/0012* (2013.01); *C12P 7/40* (2013.01); *C12P 13/04* (2013.01); *C12P 13/22* (2013.01); *C12P 41/006* (2013.01); *C12N 15/70* (2013.01); *C12N 15/74* (2013.01)

(58) Field of Classification Search
CPC .... C12N 9/0012; C12N 9/0016; C12N 15/70; C12Y 206/01; C12Y 104/99003
USPC ...................... 435/320.1, 252.3, 252.33, 189; 536/23.2
See application file for complete search history.

(56) References Cited

U.S. PATENT DOCUMENTS

| 4,590,161 A | 5/1986 | Kula et al. |
| 4,849,345 A | 7/1989 | Asano et al. |
| 4,970,157 A | 11/1990 | Hibino et al. |
| 5,416,019 A | 5/1995 | Leuchtenberger et al. |
| 5,851,810 A * | 12/1998 | Blanchard ..................... 435/189 |
| 2006/0063238 A1 | 3/2006 | Hummel et al. |
| 2009/0209012 A1 | 8/2009 | Hayashi et al. |
| 2011/0086396 A1 | 4/2011 | Kanamaru et al. |

FOREIGN PATENT DOCUMENTS

| EP | 0188712 | 7/1986 |
| EP | 1900821 | 3/2008 |
| EP | 1918375 | 5/2008 |
| JP | 59-198972 | 11/1984 |
| JP | 61-146183 | 7/1986 |
| JP | 61-239887 | 10/1986 |
| JP | 63-32482 | 2/1988 |
| JP | 63-157986 | 6/1988 |
| JP | 63-304980 | 12/1988 |
| JP | 2007-522810 | 8/2007 |
| JP | 2008-048628 | 3/2008 |
| WO | 2005090590 | 9/2005 |
| WO | 2006/132145 A1 | 12/2006 |
| WO | 2007/015511 A1 | 2/2007 |
| WO | 2008029921 | 3/2008 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Sekine et al Environ Microbiol 2006, 8, pp. 334-346.*
International Search Report for International Application No. PCT/JP2009/006679 mailed on Jan. 12, 2010.
International Preliminary Report on Patentability for International Application No. PCT/JP2009/006679 mailed on Jul. 5, 2011.
Xu, et al. *Rhodococcus qingshengii* sp. nov., a carbendazim-degrading bacterium, Int. J. System. Evol. Microbiol., 2007, vol. 57, pp. 2754-2757.

(Continued)

*Primary Examiner* — Tekchand Saidha
*Assistant Examiner* — Md. Younus Meah
(74) *Attorney, Agent, or Firm* — Amin, Turocy & Watson, LLP

(57) ABSTRACT

The present invention relates to a novel amino acid dehydrogenase, DNA encoding the enzyme, and a transformant having the DNA introduced therein. The present invention also relates to a process for producing an L-amino acid, 2-oxo acid or D-amino acid, which includes allowing the amino acid dehydrogenase or a microorganism or transformant capable of producing the enzyme to act on a substrate compound. The amino acid dehydrogenase has good reactivity even with an amino acid or a 2-oxo acid each having a bulky side chain such as an aromatic-ring-containing group, which acids are poorly reactive with conventional amino acid dehydrogenases. The amino acid dehydrogenase enables the inexpensive and highly efficient production of a useful optically active amino acid.

6 Claims, 2 Drawing Sheets

(56) References Cited

OTHER PUBLICATIONS

Brunhuber, et al. Cloning, Sequencing, and Expression of Rhodococcus L-Phenylalanine Dehydrogenase, J. Biol. Chem., 1994, vol. 269, No. 23, pp. 16203-16211.

Hummel, et al. Isolation of L-phenylalanine dehydrogenase from *Rhodococcus* sp. M4 and its application for the production of L-phenylalanine, Appl. Microbiol. Biotechnol., 1987, vol. 26, pp. 409-416.

Misono, et al. Purification and Characterization of a Dimeric Phenylalanine Dehydrogenase from Rhodococcus maris K-18, Journal of Bacteriology, vol. 171(1), pp. 30-36, 1989.

Asano. Development of New Microbial Enzymes and Their Use in Organic Synthesis, Journal of Synthetic Organic Chemistry, Japan, vol. 47, No. 8, pp. 749-759, 1989.

Asano, et al. Thermostable phenylalanine dehydrohenase from a mesophilic *Microbacterium* sp. strain DM 86-1, Arch. Microbiol., vol. 169, pp. 220-224, 1998.

Asano, et al. Novel Phenylalanine Dehydrogenases from Sporosarcina ureae and Bacillus sphaericus, J. of Biological Chemistry, vol. 262(21), pp. 10346-10354, 1987.

Asano, et al. Phenylalanine dehydrogenase of Bacillus badius, Eur. J. Biochem., vol. 168, pp. 153-159, 1987.

Asano, et al. Bacillus Phenylalanine Dehydrogenase Produced in *Escherichia coli*—Its Purification and Application to L-Phenylalanine Synthesis, Agric. Biol. Chem., vol. 51, pp. 2621-2623, 1987.

Takada, et al. Thermostable Phenylalanine Dehydrogenase of Thermoactinomyces internedius: Cloning, Expression, and Sequencing of Its Gene, J. Biochem., vol. 109(3), pp. 371-376, 1991.

Asano, et al. Enantioselective Synthesis of (5)-Amino Acids by Phenylalanine Dehydrogenase from Bacillus sphaericus: Use of Natural and Recombinant Enzymes, J. Org. Chem., vol. 55, pp. 5567-5571, 1990.

Patel. Enzymatic synthesis of chiral intermediates for Omapatrilat, and antihypertensive drug, Biomolecular Engineering, vol. 17, pp. 167-182, 2001.

Nakajima, et al. Enzymatic Conversion of Racemic Methionine to the L-Enantiomer, J. Chem. Soc.: Chem. Commun., vol. 13, pp. 947-948, 1990.

Stephen Y.K. Seah, et al., Alteration in Relative Activities of Phenylalanine Dehydrogenase Towards Different Substrates by Site-directed Mutagenesis, FEBS Letters 370, Jul. 1995, p. 93-96.

* cited by examiner

AMINO ACID DEHYDROGENASE, AND PROCESS FOR PRODUCING L-AMINO ACID, 2-OXO ACID OR D-AMINO ACID

TECHNICAL FIELD

The present invention relates to a novel, microbially produced amino acid dehydrogenase, to a DNA encoding this novel amino acid dehydrogenase, and to a process for producing an amino acid dehydrogenase using a microorganism or transformant capable of producing the amino acid dehydrogenase, and further to an efficient process for producing an L-amino acid, 2-oxo acid or D-amino acid using an amino acid dehydrogenase.

BACKGROUND ART

Amino acid dehydrogenases are enzymes that engage in the coenzyme-dependent catalysis of the reductive amination reaction of a 2-oxo acid and the reverse reaction, i.e., the oxidative deamination reaction of an amino acid. For example, amino acid dehydrogenases are known to have an industrially useful activity, e.g., the highly stereoselective production of an L-amino acid from a 2-oxo acid in the presence of ammonia and a coenzyme. L-amino acids are useful for foods and feed, and as synthesis intermediates for agrichemicals, industrial reagents, cosmetics, pharmaceuticals and the like, and are also important in organic synthesis as optical resolution agents and chiral building blocks.

Examples of amino acid dehydrogenases include phenylalanine dehydrogenase (enzyme number EC1.4.1.20) and leucine dehydrogenase (enzyme number EC1.4.1.9). Examples of microorganisms known to produce phenylalanine dehydrogenase include *Rhodococcus* sp. (Patent Document 1), *Rhodococcus maris* (Non-patent Document 1), *Bacillus badius* (Patent Document 2), *Bacillus sphaericus* (Non-patent Document 2), *Microbacterium* sp. (Non-patent Document 3), *Thermoactinomyces intermedius* (Patent Document 3), *Brevibacterium* sp. (Patent Document 4), and *Sporosarcina ureae* (Patent Document 5, Non-patent Document 4).

Amino acid dehydrogenases are classified according to differences in the types of compounds with which the enzymes readily react. For example, leucine dehydrogenase exhibits good activity for branched-chain amino acids such as L-leucine, L-valine, and L-isoleucine, short-chain straight-chain amino acids such as L-norvaline, and the corresponding 2-oxo acids, but exhibits almost no activity for aromatic amino acids such as L-phenylalanine and L-tyrosine and the corresponding 2-oxo acids. In contrast, phenylalanine dehydrogenase is known to exhibit good activity for the aforementioned aromatic amino acids and the corresponding 2-oxo acids, i.e., phenylpyruvic acid and 4-hydroxyphenylpyruvic acid. However, the phenylalanine dehydrogenases known to date exhibit a weaker activity for 2-oxo acids that have a large side chain structure, e.g., naphthylpyruvic acid and homophenylpyruvic acid, than for phenylpyruvic acid (Non-patent Document 2, Non-patent Document 3). Unnatural amino acids such as L-2-naphthylalanine and L-homophenylalanine are useful as synthesis intermediates for agrichemicals, industrial reagents, cosmetics, pharmaceuticals and the like.

Phenylalanine dehydrogenase gene expression by a transformant is known, for example, for genes originating from *Rhodococcus* sp. (Non-patent Document 5), *Bacillus badius* (Non-patent Document 6), *Bacillus sphaericus* (Non-patent Document 7), *Sporosarcina ureae* (Patent Document 6), and *Thermoactinomyces intermedius* (Non-patent Document 8).

A reaction that converts a 2-oxo acid into an L-amino acid by the action on the 2-oxo acid of a coenzyme-regenerating enzyme and a phenylalanine dehydrogenase originating from *Rhodococcus* sp., *Bacillus sphaericus*, or *Thermoactinomyces intermedius* is already known (Patent Document 1, Non-patent Document 9, and Non-patent Document 10).

A reaction that converts a D-amino acid, via a 2-oxo acid or an imino acid, into an L-amino acid by the action on a racemic amino acid of bovine liver-derived glutamate dehydrogenase or *Clostridium thermoaceticum*-derived leucine dehydrogenase in combination with D-amino acid oxidase and a coenzyme-regenerating enzyme is also already known (Non-patent Document 10, Non-patent Document 11).

Patent Document 1: Japanese Patent Application Laid-open No. S61-146183
Patent Document 2: Japanese Patent Application Laid-open No. S63-32482
Patent Document 3: Japanese Patent Application Laid-open No. S63-304980
Patent Document 4: Japanese Patent Application Laid-open No. S59-198972
Patent Document 5: Japanese Patent Application Laid-open No. S61-239887
Patent Document 6: Japanese Patent Application Laid-open No. S63-157986
Non-patent Document 1: *Journal of Bacteriology*, Vol. 171 (1), p. 30 (1989)
Non-patent Document 2: *Journal of Synthetic Organic Chemistry*, Japan, Vol. 47, No. 8, p. 749 (1989)
Non-patent Document 3: *Arch. Microbiol.*, Vol. 169, p. 220 (1998)
Non-patent Document 4: *J. of Biological Chemistry*, Vol. 262(21), p. 10346 (1987)
Non-patent Document 5: *J. of Biological Chemistry*, Vol. 269(23), p. 16203 (1994)
Non-patent Document 6: *Eur. J. Biochem.*, Vol. 168, p. 153 (1987)
Non-patent Document 7: *Agric. Biol. Chem.*, Vol. 51, p. 2621 (1987)
Non-patent Document 8: *J. Biochem.*, Vol. 109(3), p. 371 (1991)
Non-patent Document 9: *J. Org. Chem.*, Vol. 55, p. 5567 (1990)
Non-patent Document 10: *Biomolecular Engineering*, Vol. 17, p. 167 (2001)
Non-patent Document 11: *J. Chem. Soc.: Chem. Commun.*, Vol. 13, p. 947 (1990)

SUMMARY OF THE INVENTION

An object of the present invention is to provide a novel amino acid dehydrogenase that exhibits a high activity not only for phenylpyruvic acid, but also for 2-oxo acids such as, for example, naphthylpyruvic acid and homophenylpyruvic acid, which, due to their large side chains, exhibit a low reactivity with the heretofore known amino acid dehydrogenases. A further object of the present invention is to provide, by identifying the amino acid sequence of this amino acid dehydrogenase and the DNA sequence of its gene, a microorganism or transformant capable of producing the enzyme and a process for producing the amino acid dehydrogenase using the microorganism or transformant. A further object of the present invention is to provide an efficient process for producing an L-amino acid, 2-oxo acid or D-amino acid using the amino acid dehydrogenase.

In view of these challenges, the present inventors searched a broad range of soils for microorganisms that had an amino acid dehydrogenase activity and as a result were able to separate for the first time a *Rhodococcus* bacterium that had a strong ability to produce an amino acid dehydrogenase that had excellent and novel properties. The present inventors also achieved the isolation and purification of the amino acid dehydrogenase from this microorganism and the isolation of the amino acid dehydrogenase gene and its expression in a host microorganism. The production of an L-amino acid, 2-oxo acid or D-amino acid was also made possible by the action on a 2-oxo acid, racemic amino acid or L-amino acid of the amino acid dehydrogenase obtained in the present invention, either alone or in combination with a coenzyme-regenerating enzyme. The present invention was accomplished as a consequence of the preceding. In addition, the production of an L-amino acid was also made possible by the action on a racemic amino acid or D-amino acid of the amino acid dehydrogenase obtained in the present invention in combination with a D-amino acid oxidase and a coenzyme-regenerating enzyme. The present invention was also accomplished as a consequence of the preceding.

The present invention has the following single or plurality of features.

1) The present invention is a DNA according to any of the following (a), (b), (c), (d), (e) and (f):

(a) a DNA encoding a polypeptide comprising the amino acid sequence shown in Sequence Listing SEQ ID NO:1;

(b) a DNA encoding a polypeptide that has an amino acid dehydrogenase activity and comprises an amino acid sequence provided by the substitution, insertion, deletion and/or addition of one or a plurality of amino acids in the amino acid sequence shown in Sequence Listing SEQ ID NO:1;

(c) a DNA encoding a polypeptide that has an amino acid dehydrogenase activity and comprises an amino acid sequence that has at least 70% sequence identity with the amino acid sequence shown in Sequence Listing SEQ ID NO:1;

(d) a DNA comprising the base sequence shown in Sequence Listing SEQ ID NO:2;

(e) a DNA that encodes a polypeptide having an amino acid dehydrogenase activity and has a base sequence provided by the substitution, insertion, deletion and/or addition of one or a plurality of bases in the base sequence shown in Sequence Listing SEQ ID NO:2; and (f) a DNA that encodes a polypeptide having an amino acid dehydrogenase activity and comprises a base sequence that has at least 70% sequence identity with the base sequence shown in Sequence Listing SEQ ID NO:2.

2) The present invention is a polypeptide according to any of the following (g), (h) and (i):

(g) a polypeptide comprising the amino acid sequence shown in Sequence Listing SEQ ID NO:1;

(h) a polypeptide that has an amino acid dehydrogenase activity and comprises an amino acid sequence provided by the substitution, insertion, deletion and/or addition of one or a plurality of amino acids in the amino acid sequence shown in Sequence Listing SEQ ID NO:1; and (i) a polypeptide that has an amino acid dehydrogenase activity and comprises an amino acid sequence that has at least 70% sequence identity with the amino acid sequence shown in Sequence Listing SEQ ID NO:1.

3) The present invention is a polypeptide that has an amino acid dehydrogenase activity; exhibits activity for a 2-oxo acid represented by general formula (1):

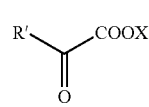

wherein R' represents an optionally substituted $C_{5-20}$ alkyl group, an optionally substituted $C_{5-20}$ alkenyl group, an optionally substituted $C_{5-20}$ alkynyl group, an optionally substituted $C_{4-20}$ aryl group, or an optionally substituted $C_{5-20}$ aralkyl group, and X represents a hydrogen atom, an alkali metal or an alkaline-earth metal; and exhibits an activity for naphthylpyruvic acid that is at least one-fiftieth of an activity thereof for phenylpyruvic acid.

4) The present invention is the aforementioned polypeptide in which R' in general formula (1) is an indolylmethyl group or phenylethyl group.

5) The present invention is the aforementioned polypeptide which originates from *Rhodococcus*.

6) The present invention is a recombinant plasmid that contains the aforementioned DNA.

7) The present invention is a transformant obtained by transforming a host microorganism with the aforementioned recombinant plasmid.

8) The present invention is a transformant obtained by transforming with the aforementioned DNA and a DNA encoding a chaperone.

9) The present invention is a microorganism that is capable of producing the aforementioned polypeptide and belongs to the genus *Rhodococcus*.

10) The present invention is a process for producing an amino acid dehydrogenase, comprising:

culturing a microorganism capable of producing the aforementioned polypeptide;

accumulating the polypeptide in the culture; and recovering the polypeptide.

11) The present invention is a process for producing an L-amino acid represented by general formula (3):

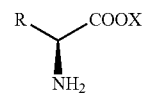

wherein R represents an optionally substituted $C_{1-20}$ alkyl group, an optionally substituted $C_{2-20}$ alkenyl group, an optionally substituted $C_{2-20}$ alkynyl group, an optionally substituted $C_{4-20}$ aryl group, or an optionally substituted $C_{5-20}$ aralkyl group, and X represents a hydrogen atom, an alkali metal or an alkaline-earth metal, by allowing the aforementioned polypeptide (a polypeptide that has an amino acid dehydrogenase activity), the aforementioned transformant, or the aforementioned microorganism to act on a 2-oxo acid represented by general formula (2):

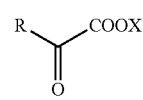

wherein R and X are defined as above.

11) The present invention is a process for producing an L-amino acid represented by general formula (3):

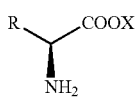

(3)

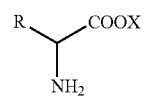

(4)

wherein R and X are defined as above, by allowing the aforementioned polypeptide (a polypeptide that has an amino acid dehydrogenase activity), the aforementioned transformant, or the aforementioned microorganism to act, in the presence of a D-amino acid oxidase, on a racemic amino acid represented by general formula (4):

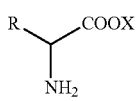

(4)

wherein R and X are defined as above, or a D-amino acid represented by general formula (5):

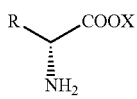

(5)

wherein R and X are defined as above.

12) The present invention is a process for producing a 2-oxo acid represented by general formula (2):

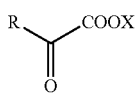

(2)

wherein R and X are defined as above, or a D-amino acid represented by general formula (5):

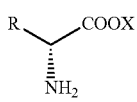

(5)

wherein R and X are defined as above, by allowing the aforementioned polypeptide (a polypeptide that has an amino acid dehydrogenase activity), or the aforementioned transformant, or the aforementioned microorganism to act on an L-amino acid represented by general formula (3):

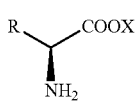

(3)

wherein R and X are defined as above, or a racemic amino acid represented by general formula (4):

wherein R and X are defined as above.

The present invention, comprising the features described above, enables efficient production of a novel amino acid dehydrogenase that exhibits a high reactivity for substrates for which the heretofore reported amino acid dehydrogenases have a low activity. In addition, the present invention enables efficient production of an L-amino acid, 2-oxo acid or D-amino acid by using the amino acid dehydrogenase, or a transformant or microorganism capable of producing the amino acid dehydrogenase.

BEST MODE FOR CARRYING OUT THE INVENTION

Figure 1:
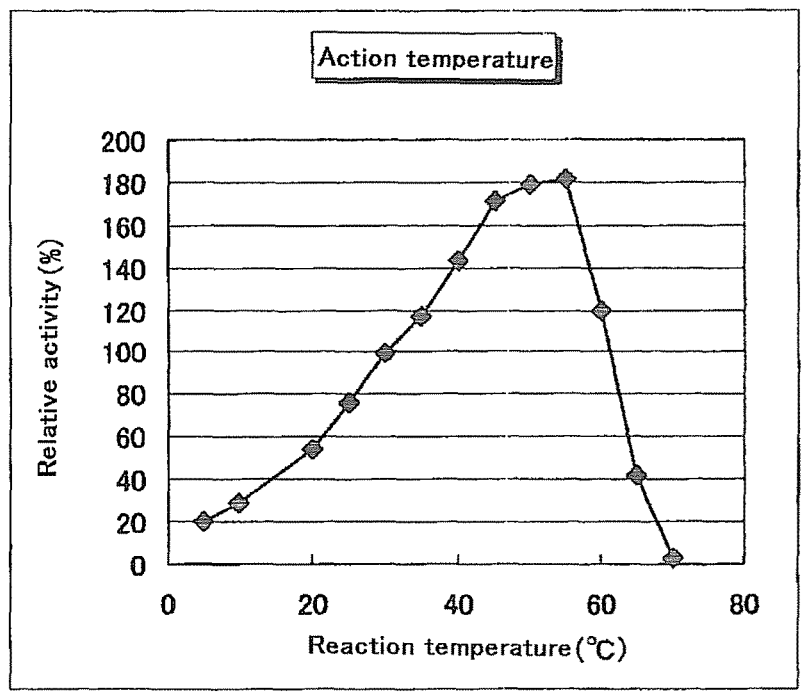
FIG. 1 is a graph that shows the relationship between the relative activity and the action temperature (including the optimal temperature) for an amino acid dehydrogenase according to an embodiment of the present invention.

The present invention is described in detail below based on embodiments. The scope of the invention is not limited by the embodiments or by the working examples.

1. Polypeptide

A description will first be provided for a polypeptide that is an embodiment of the present invention. The polypeptide according to the embodiment is characteristically a polypeptide that has an amino acid dehydrogenase activity and has the following physical-chemical properties.

1) Activity

The polypeptide reductively aminates a 2-oxo acid in the presence of ammonia and a coenzyme to produce an L-amino acid. Or, the polypeptide oxidatively deaminates an L-amino acid in the presence of a coenzyme to produce a 2-oxo acid and ammonia.

2) Molecular Weight

Molecular weight: approximately 94,000

Subunit molecular weight: approximately 46,000

3) Action Temperature Range

Temperature range: at least approximately 5° C. to approximately 70° C.

Optimal temperature: approximately 45° C. to approximately 50° C.

The temperature range denotes the temperature range in which the enzyme has a suitable activity, while the optimal temperature denotes the temperature at which the enzyme exhibits the most favorable activity. The enzyme under consideration also exhibits activity at temperatures outside the temperature range given above.

4) Action pH Range pH range: at least approximately 7.1 to approximately 11.0

Optimal pH: approximately 8.8 to approximately 10.0

The pH range denotes the pH range in which the enzyme has a suitable activity, while the optimal pH denotes the pH at which the enzyme exhibits the most favorable activity. The enzyme under consideration also exhibits activity at pH values outside the range given above.

5) Specific Activity 204 units (30° C.) per 1 mg of pure enzyme.

1 unit is defined as the quantity of enzyme that consumes 1 μmol NADH in 1 minute.

6) Substrate Specificity

Considered relative to phenylpyruvic acid, the activity for 2-oxo acids that have a large side chain structure, e.g., naphthylpyruvic acid, indolepyruvic acid, and homophenylpyruvic acid, is also high. This high activity is at least one-fiftieth, preferably at least one-twenty fifth, and more preferably at least one-tenth, of the activity for phenylpyruvic acid.

The 2-oxo acid that has a large side chain structure refers to a 2-oxo acid with general formula (1) in which R' represents an optionally substituted $C_{5-20}$ alkyl group, an optionally substituted $C_{5-20}$ alkenyl group, an optionally substituted $C_{5-20}$ alkynyl group, an optionally substituted $C_{4-20}$ aryl group, or an optionally substituted $C_{5-20}$ aralkyl group.

The optionally substituted $C_{5-20}$ alkyl group for R' is not particularly limited and can be exemplified by pentanyl, hexanyl, heptanyl, or octanyl.

The optionally substituted $C_{5-20}$ alkenyl group is not particularly limited and can be exemplified by pentenyl, hexenyl, heptenyl, or octenyl.

The optionally substituted $C_{5-20}$ alkynyl group is not particularly limited and can be exemplified by pentynyl, hexynyl, heptynyl, or octynyl.

The optionally substituted $C_{4-20}$ aryl group is not particularly limited and can be exemplified by phenyl, 4-hydroxyphenyl, anthranyl, pyridyl, pyrimidyl, indanyl, indenyl, or naphthyl.

The optionally substituted $C_{5-20}$ aralkyl group is not particularly limited and can be exemplified by indolylmethyl, naphthylmethyl, anthranylmethyl, indanylmethyl, indenylmethyl, phenylethyl, phenylpropyl, phenylbutyl, or diphenylmethyl.

The substituent can be exemplified by amino, hydroxyl, nitro, cyano, carboxyl, alkyl, aralkyl, aryl, alkanoyl, alkenyl, alkynyl, alkoxyl, or halogen atom.

X represents a hydrogen atom, an alkali metal or an alkaline-earth metal and is not particularly limited and examples thereof include a hydrogen atom, lithium, sodium, potassium, magnesium, and calcium.

Based on its substrate specificity, the amino acid dehydrogenase of this embodiment is classified as a phenylalanine dehydrogenase (enzyme number EC1.4.1.20). It has different properties from the other phenylalanine dehydrogenases, for example, as shown below.

(a) The *Rhodococcus* sp.-derived phenylalanine dehydrogenase (Patent Document 1, Non-patent Document 5), which has a homotetrameric structure composed of subunits with a molecular weight of 39,500, has a substantially different enzyme molecular weight and structure. The amino acid sequence is also substantially different (66.9% amino acid sequence identity). The enzymatic activity ratios are also substantially different since the enzymatic activities for indolepyruvic acid and 4-hydroxyphenylpyruvic acid are 3 and 5, respectively, taking the enzymatic activity for phenylpyruvic acid to be 100.

(b) The *Rhodococcus maris*-derived phenylalanine dehydrogenase (Non-patent Document 1), which has a homodimeric structure composed of subunits with a molecular weight of 36,000, has a substantially different enzyme molecular weight. The enzymatic activity ratios are also substantially different since the enzymatic activities for indolepyruvic acid and 2-oxo-4-(methylthio)butanoic acid are 5 and 9, respectively, taking the enzymatic activity for phenylpyruvic acid to be 100.

(c) The *Bacillus badius*-derived phenylalanine dehydrogenase (Non-patent Document 2, Non-patent Document 6), which has a homooctameric structure composed of subunits with a molecular weight of 41,000 to 42,000, has a substantially different enzyme molecular weight and structure. The amino acid sequence is also substantially different (36.1% amino acid sequence identity).

(d) The *Bacillus sphaericus*-derived phenylalanine dehydrogenase (Non-patent Document 2, Non-patent Document 7), which has a homooctameric structure composed of subunits with a molecular weight of 39,000, has a substantially different enzyme molecular weight and structure. The amino acid sequence is also substantially different (36.6% amino acid sequence identity). The enzymatic activity ratios are also substantially different since the enzymatic activities for naphthylpyruvic acid, homophenylpyruvic acid, and indolepyruvic acid are 0.46, 3.4, and 0.39, respectively, taking the enzymatic activity for phenylpyruvic acid to be 100.

(e) The *Microbacterium* sp.-derived phenylalanine dehydrogenase (Non-patent Document 3), which has a homooctameric structure composed of subunits with a molecular weight of 41,000, has a substantially different enzyme molecular weight and structure. The enzymatic activity ratio is also substantially different since the enzymatic activity for homophenylpyruvic acid is 0.1 taking the enzymatic activity for phenylpyruvic acid to be 100.

(f) The *Thermoactinomyces intermedius*-derived phenylalanine dehydrogenase (Patent Document 3, Non-patent Document 8), which has a homohexameric structure composed of subunits with a molecular weight of 41,000, has a substantially different enzyme molecular weight and structure. The amino acid sequence is also substantially different (32.9% amino acid sequence identity). The enzymatic activity ratio is also substantially different since the enzymatic activity for 4-hydroxyphenylpyruvic acid is 0 taking the enzymatic activity for phenylpyruvic acid to be 100.

(g) The *Brevibacterium* sp.-derived phenylalanine dehydrogenase (Patent Document 4), which has a homodimeric structure composed of subunits with a molecular weight of 66,000±5000, has a substantially different enzyme molecular weight. The specific activity of the pure enzyme is also substantially different.

(h) The *Sporosarcina ureae*-derived phenylalanine dehydrogenase (Patent Document 5, Non-patent Document 4), which has a homooctameric structure composed of subunits with a molecular weight of 39,000, has a substantially different enzyme molecular weight and structure. The amino acid sequence is also substantially different (35.4% amino acid sequence identity). The enzymatic activity ratio is also substantially different since the enzymatic activity for indolepyruvic acid is 0.73 taking the enzymatic activity for phenylpyruvic acid to be 100.

The "sequence identity" in the embodiments can be determined using, for example, a method well known to those skilled in the art, sequence analysis software, and so forth. For example, a homology search with GENETYX Ver. 7 genetic information processing software/Windows edition, from GENETYX Corporation, was used here.

2. Measurement of Amino Acid Dehydrogenase Activity

In the embodiments, the amino acid dehydrogenase activity of the polypeptide can be measured, for example, based on the rate of decline in the absorbance at a wavelength of 340 nm when 1.2 mL of 0.5 M NH3/NH4Cl buffer (pH 9.0), 0.2 mL of 0.1 M sodium carbonate buffer (pH 9.0) containing 3 mM NADH coenzyme, and 0.1 mL of an appropriately diluted enzyme solution are added to 1.5 mL of 0.1 M sodium carbonate buffer (pH 9.0) containing 10 mM phenylpyruvic acid as substrate and a reaction is run for 1 minute at 30° C. In the embodiments, the amino acid dehydrogenase activity was measured using this method unless indicated otherwise.

3. Microorganism

The polypeptide of the embodiment can be acquired from a microorganism that has an amino acid dehydrogenase activity. While there are no particular limitations other than that the microorganism has the ability to produce this polypeptide, examples thereof include microorganisms belonging to the genus *Rhodococcus*, and among these, *Rhodococcus qingshengii* is preferred and *Rhodococcus qingshengii* strain KNK2108 is more preferred.

The *Rhodococcus qingshengii* strain KNK2108 is a strain isolated and acquired by the inventors of the present invention and was deposited at the International Patent Organism Depositary, National Institute of Advanced Industrial Science and Technology (Tsukuba Central 6, 1-1-1 Higashi, Tsukuba-shi, Ibaraki, 305-8566, Japan) on 26 Nov. 2008 under accession number FERM BP-11067.

The bacteriological characteristics of *Rhodococcus qingshengii* strain KNK2108 are given below.

1. Form
1) *bacillus*
   rod-coccus cycle (+)
   24 hour: approximately diameter 0.7 to 0.8 μm×1.5 to 2.5 μm
   72 hour: approximately diameter 0.6 to 0.7 μm×1.0 to 1.2 μm
2) Gram stain: positive
3) motility: negative
4) sporulation: negative
5) colony morphology by flat agar medium culture: circular shape, margin entire, hemispherical, smooth surface, opaque, butyrous consistency, light orange 2. Culture Properties
1) Growth temperature test: 37° C. (+), 45° C. (−)

3. Physiological Properties
1) catalase reaction: +
2) oxidase reaction: −
3) acid/gas production from glucose (acid production/gas production): −/−
4) O/F test (oxidation/fermentation): −/−
5) Fermentation tests
glucose: −
ribose: −
xylose: −
mannitol: −
maltose: −
lactose: −
sucrose: −
glycogen: −
6) Biochemical tests
nitrate reduction: −
pyrazine amidase: −
pyrrolidonyl arylamidase: −
alkaline phosphatase: +
β-glucuronidase: −
β-galactosidase: −
α-glucosidase: +
N-acetyl-β-glucosaminidase: −
esculin (β-glucosidase): −
urease: +
gelatin hydrolysis: −
7) Anaerobic growth: −
8) Starch hydrolysis: −
9) MR (Methyl Red test): −
10) VP (acetoin production): −

The KNK2108 strain was identified as *Rhodococcus qingshengii* based on the bacteriological characteristics given above and 16S rDNA sequence analysis.

The microorganism that produces the polypeptide of the embodiment may be the wild-type strain of a microorganism mentioned above or may be a mutant strain as provided by mutational modification. The mutant strain can be acquired by a method well known to those skilled in the art, for example, exposure to UV or treatment with a reagent such as N-methyl-N'-nitro-N-nitrosoguanidine (NTG), ethyl methanesulfonate (EMS), and so forth.

The medium used to culture the microorganism that produces the polypeptide of the present invention should enable the growth of the microorganism but is not otherwise particularly limited. For example, an ordinary liquid medium can be used that contains a carbon source such as a carbohydrate such as glucose or sucrose, an alcohol such as ethanol or glycerol, a fatty acid such as oleic acid or stearic acid or a fatty acid ester, or an oil such as rapeseed oil or soy oil; a nitrogen source such as ammonium sulfate, sodium nitrate, peptone, casamino acids, corn steep liquor, bran, or yeast extract; an inorganic salt such as magnesium sulfate, sodium chloride, calcium carbonate, dipotassium hydrogen phosphate, or potassium dihydrogen phosphate; and other nutrient sources such as malt extract, meat extract, and so forth.

A substance that increases the production of the amino acid dehydrogenase, e.g., an amino acid or amino acid derivative, may also be added in small quantities. The concentration in the medium of this substance that increases amino acid dehydrogenase production is selected from the range of at least 0.001% by weight to not more than 10% by weight and preferably from the range of at least 0.01% by weight to not more than 1% by weight.

Cultivation is generally carried out aerobically and can be performed using a temperature range from at least 10° C. to not more than 60° C. and preferably from at least 20° C. to not more than 50° C. and a pH range from at least 3 to not more than 11 and preferably from at least 5 to not more than 9, for a cultivation time of from about at least 1 day to about not more than 5 days. The cultivation method may be a batch or continuous method.

After the completion of cultivation, the cells may be collected from the culture by, for example, centrifugal separation, and may be disrupted by a means such as, for example, ultrasound disruption, to obtain a crude enzyme solution. The polypeptide of the present invention can be obtained by subjecting this crude enzyme solution to purification by, for example, salting out, column chromatography, and so forth.

4. Amino Acid Sequence

The polypeptide of the present invention may be a naturally occurring enzyme acquired from a microorganism as described above or may be a recombinant enzyme produced using recombinant DNA technology. The polypeptide shown by SEQ ID NO:1 in the Sequence Listing is an example of the naturally occurring enzyme.

The polypeptide that is an embodiment of the present invention may also be a polypeptide that has an amino acid dehydrogenase activity and comprises an amino acid sequence provided by the substitution, insertion, deletion and/or addition of one or a plurality of amino acids in the amino acid sequence shown in Sequence Listing SEQ ID NO:1, or may be a polypeptide that has an amino acid dehydrogenase activity and comprises an amino acid sequence that has at least 70%, or at least 75%, or at least 80%, or at least 85%, or at least 90%, or at least 95%, and more preferably at least 99% homology with the amino acid sequence given by SEQ ID NO:1. The "plurality of amino acids" is not limited as to the actual number as long as the amino acid dehydrogenase activity is not lost, and can be exemplified by not more than 25 amino acids, preferably not more than 20 amino acids, more preferably not more than 15 amino acids, even more preferably not more than 10 amino acids, and most preferably not more than 5, 4, 3, or 2 amino acids.

The "polypeptide that has an amino acid dehydrogenase activity" denotes a polypeptide that has an activity that is at least 10%, preferably at least 40%, more preferably at least 60%, and even more preferably at least 80%, of the activity of a polypeptide comprising the amino acid sequence shown in SEQ ID NO:1 under the aforementioned activity measurement conditions.

5. DNA

"DNA" that is an embodiment of the present invention will now be described. The DNA of the present invention may be a DNA that encodes a polypeptide as described above. It may be the DNA shown by SEQ ID NO:2 of the Sequence Listing or may be a DNA that encodes a polypeptide having an amino acid dehydrogenase activity and has a base sequence provided by the substitution, insertion, deletion and/or addition of one or a plurality of bases in the base sequence shown in Sequence Listing SEQ ID NO:2. The "plurality of bases" is not limited as to the actual number as long as the polypeptide encoded by the DNA does not lose its amino acid dehydrogenase activity, and can be exemplified by preferably not more than 50 bases, more preferably not more than 30 bases, even more preferably not more than 20 bases, and most preferably not more than 10, 9, 8, 7, 6, 5, 4, 3, or 2 bases.

This DNA may also be a DNA that encodes a polypeptide having an amino acid dehydrogenase activity and comprises a base sequence that has at least 70%, preferably at least 75%, at least 80%, at least 85%, at least 90%, or at least 95%, and more preferably at least 99% homology with the base sequence given by SEQ ID NO:2.

The DNA of the present invention may also be a DNA that encodes a polypeptide having an amino acid dehydrogenase activity and hybridizes under stringent conditions with a DNA comprising a base sequence complementary to the base sequence shown in Sequence Listing SEQ ID NO:2.

The "DNA that hybridizes under stringent conditions with a DNA comprising a base sequence complementary to the base sequence shown in Sequence Listing SEQ ID NO:2" denotes a DNA that can specifically form a hybrid with a DNA comprising a base sequence complementary to the base sequence shown in Sequence Listing SEQ ID NO:2 through execution of, for example, the colony hybridization method, plaque hybridization method, or Southern hybridization method.

Here, the stringent conditions denote, for example, the following conditions: hybridization at 65° C. in an aqueous solution with the composition of 75 mM trisodium citrate, 750 mM sodium chloride, 0.5% sodium dodecyl sulfate, 0.1% bovine serum albumin, 0.1% polyvinylpyrrolidone, and 0.1% Ficoll 400 (from Amersham Biosciences), followed by washing at 60° C. using an aqueous solution with the composition of 15 mM trisodium citrate, 150 mM sodium chloride, and 0.1% sodium dodecyl sulfate. Hybridization under the conditions given above is preferably followed by washing at 65° C. using an aqueous solution with the composition of 15 mM trisodium citrate, 150 mM sodium chloride, and 0.1% sodium dodecyl sulfate and more preferably is followed by washing at 65° C. using an aqueous solution with the composition of 1.5 mM trisodium citrate, 15 mM sodium chloride, and 0.1% sodium dodecyl sulfate.

The DNA of the present invention (amino acid dehydrogenase gene) can be acquired from a microorganism that has an amino acid dehydrogenase activity as described above. For example, the following method can be used to acquire the desired DNA.

First, the N-terminal amino acid sequence of the amino acid dehydrogenase purified from a microorganism that has an amino acid dehydrogenase activity is determined with, for example, a gas-phase protein sequencer. In addition, after the purified amino acid dehydrogenase has been digested into polypeptides of appropriate size by the action of a protease, for example, V8 protease, the obtained polypeptides are purified using, for example, HPLC, and an internal amino acid sequence is determined using the same method as described above. DNA primers designed based on the thus obtained N-terminal amino acid sequence and internal amino acid sequence are then synthesized.

The chromosomal DNA is then isolated from a microorganism that is the source of the amino acid dehydrogenase. The chromosomal DNA can be obtained from the cultured cells using, for example, an UltraClean Microbial DNA Isolation Kit (from MO BIO Laboratories, Inc.). A part of the target gene can then be obtained by running PCR using this chromosomal DNA as a template and the previously described DNA primers.

A DNA fragment encoding the sequences outside the already obtained partial gene toward the N-terminal side and toward C-terminal side can be obtained by inverse PCR (refer, for example, to *Nucleic Acids Res.*, Vol. 16, p. 8186 (1988)). After the base sequence of the DNA fragment has been determined, DNA primers are constructed based on the DNA base sequences presumed to be upstream from the DNA encoding the N-terminal region of the enzyme and to be downstream from the DNA encoding the C-terminal region, and the DNA between these sequences is amplified by PCR using the already obtained chromosomal DNA as a template, whereby a DNA fragment containing the full length of the desired amino acid dehydrogenase gene can be obtained.

A recombinant plasmid can then be obtained by ligating the resulting DNA fragment containing the amino acid dehydrogenase gene with a vector DNA using, for example, T4 DNA ligase. Using this plasmid, the base sequence is analyzed for the vector-inserted DNA fragment region containing the amino acid dehydrogenase gene and the presence of bases encoding the N-terminal amino acid sequence and the internal amino acid sequence of the amino acid dehydrogenase is confirmed. Further, using this, the translation initiation site and the stop codon are identified, so that the open reading frame is determined.

6. Transformant and Vector

A transformant can be obtained by transforming a host microorganism using the DNA obtained by the previously described method or using the recombinant plasmid obtained by incorporating this DNA in a vector.

The host-vector systems described in Guidelines for Recombinant DNA Experiments (edited by the Science and Technology Agency, Research and Development Bureau, Life Sciences Division, revised 22 Mar. 1996) can be used for the host and vector.

For example, a microorganism of the genus *Escherichia, Pseudomonas, Flavobacterium, Bacillus, Serratia, Corynebacterium, Brevibacterium, Agrobacterium, Acetobacter, Gluconobacter, Lactobacillus, Streptococcus, Streptomyces,* or *Rhodococcus* can be used as the host.

A microbially-derived plasmid, phage, or derivative thereof capable of autonomous replication within a host as described above can be used as the vector. In particular, preferred for use are *Escherichia coli* as the host microorganism and a vector capable of autonomous replication in this microorganism as the vector. This vector can be exemplified by pUC18, pUC19, pBR322, pACYC184, pSTV28, pSTV29, pSC101, pT7Blue, and pUCNT and by derivatives of the preceding. These derivatives denote derivatives in which, with the goal of plasmid stabilization or improving the enzyme production level, for example, a gene related to regulation or the like, such as promoter, terminator, enhancer, SD sequence, or replication initiation site (ori), has been modified, or in which the chemical resistance properties or a restriction enzyme site in the cloning site has been modified.

Depending on the particular transformant, the produced enzyme may be insolubilized and may form an inclusion body. It may be possible in such cases to avoid enzyme insolubilization by changing the culture conditions, changing the host microorganism, or co-expressing the target gene and a chaperone gene in the host microorganism. The chaperone is a protein that functions in vivo to assist protein folding into the normal conformation (refer, for example, to *Appl. Biochem. Biotech.*, Vol. 66, pp. 197-238 (1997)).

The transformant *Escherichia coli* HB101 (pRPD002) is an example of a transformant. *Escherichia coli* HB101 (pRPD002) can be obtained by transformation of *Escherichia coli* HB101 with the recombinant plasmid pRPD002, itself obtained by the incorporation into pUCT (a plasmid vector obtained by the destruction of the NdeI site of pUCNT (refer to WO 94/03613)) of the DNA obtained as described above from *Rhodococcus qingshengii* strain KNK2108.

The bacteriological properties of *Escherichia coli* HB101 are described in Biochemicals for Life Science (Toyo Boseki Co., Ltd., 1993, pp. 116-119) and in various other known publications and thus are well known to those skilled in the art. *Escherichia coli* HB101 (pRPD002) has the same bacteriological properties as *Escherichia coli* HB101, in addition to having the ability to produce the specified enzyme through genetic recombination.

The recombinant DNA technology used in the present invention is well known in this field and is described, for example, in Molecular Cloning, 2nd Edition (Cold Spring Harbor Laboratory Press, 1989) and (Greene Publishing Associates and Wiley-Interscience).

7. Cultivation of Transformant and the Like

The amino acid dehydrogenase of the present invention can be produced in large amounts by the cultivation of, for example, the previously described transformant capable of producing this enzyme, and the enzyme can be used to produce an L-amino acid, 2-oxo acid or D-amino acid.

The microorganism may be cultured using an ordinary culture medium. The culture medium used for cultivation may be an ordinary culture medium that contains nutrients such as, for example, a carbon source, nitrogen source, and inorganic salts. Favorable results are frequently obtained by the addition thereto of an organic micronutrient such as vitamins, amino acids and so forth. For example, a carbohydrate such as glucose or sucrose, an organic acid such as acetic acid, or an alcohol may be appropriately used as the carbon source. For example, an ammonium salt, aqueous ammonia, gaseous ammonia, urea, yeast extract, peptone, or corn steep liquor may be used as the nitrogen source. For example, a phosphate salt, magnesium salt, potassium salt, sodium salt, calcium salt, iron salt, sulfate salt, or chloride may be used as the inorganic salt.

Cultivation can be carried out in the temperature range from 25° C. to 40° C. and particularly preferably in the temperature range from 25° C. to 37° C. Cultivation can be carried out at a pH from 4 to 8 and preferably from 5 to 7.5. The cultivation method may be a batch or continuous method.

As necessary, an enzyme induction treatment may also be carried out, for example, the addition of isopropyl-1-thio-β-D-galactoside (IPTG) or lactose.

8. Process of Producing L-Amino Acid and the Like

The efficient process of producing an L-amino acid, 2-oxo acid or D-amino acid using the amino acid dehydrogenase obtained in the embodiment will now be described. The 2-oxo acid can be obtained by the oxidation (oxidative deamination reaction) of the L-amino acid by allowing the amino acid dehydrogenase to act on the racemic amino acid or L-amino acid. The D-amino acid can be obtained as the residual substrate when the racemic amino acid is employed as the substrate in this oxidative deamination reaction. The L-amino acid can be obtained by the reductive amination (reductive amination reaction) of the 2-oxo acid by allowing the amino acid dehydrogenase to act on the 2-oxo acid. Also with reference to the L-amino acid, the D-amino acid may be oxidized to a 2-oxo acid by allowing a D-amino acid oxidase to act on the racemic amino acid or D-amino acid, and additional reaction through contact with the amino acid dehydrogenase may then be conducted to cause conversion to the L-amino acid (stereoinversion reaction).

9. D-Amino Acid Oxidase

The D-amino acid oxidase used herein is an enzyme that oxidizes a D-amino acid in the presence of oxygen with the production of a 2-oxo acid, hydrogen peroxide, and ammonia. A D-amino acid oxidase of animal, plant, or microbial origin can be used as the D-amino acid oxidase employed in the present invention, while a D-amino acid oxidase of microbial origin is preferred for industrial applications. Microorganisms capable of producing a D-amino acid oxidase can be exemplified by the following, which are known microorganisms capable of producing this enzyme: the genera *Arthrobacter, Aspergillus, Candida, Cryptococcus, Curvularia, Exophiala, Fusarium, Gibberella, Hansenula, Kloeckera, Kluyveromyces, Neurospora, Pichia, Rhodosporidium, Rhodotorula, Sporobolomyces, Trigonopsis, Verticillium,* and *Yarrowia.*

An enzyme derived from a microorganism of the genus *Candida* is preferred. In particular, an enzyme derived from *Candida intermedia* is preferred and an enzyme derived from *Candida intermedia* strain NBRC0761 is more preferred.

As is well known, the production of a transformed microorganism is effective for obtaining a highly active microorganism that is a strong and efficient producer of D-amino acid oxidase. In an example of a method for producing such a transformed microorganism, as described in WO 07/015,511, the D-amino acid oxidase gene from a strain that exhibits a D-amino acid oxidase activity is cloned; a recombinant plasmid is then constructed using an appropriate vector; and this recombinant plasmid is used to transform an appropriate host microorganism. The recombinant DNA technology is well known in this field.

The thus obtained transformant that is a strong producer of D-amino acid oxidase can be exemplified by *Escherichia coli* HB101 (pCDA003) (FERN BP-10639) and *Escherichia coli* JM109 (pCDA003) (FERN BP-10638), which are described in WO 07/015,511 and contain the D-amino acid oxidase gene from *Candida intermedia* strain NBRC0761.

The production of D-amino acid oxidase by these transformants or by the previously referenced strains having a D-amino acid oxidase activity may be carried out, for example, as described in WO 07/015,511, by cultivation using an ordinary nutrient media; an enzyme induction treatment may also be carried out as necessary.

10. Coenzyme Regeneration System

The amino acid dehydrogenase-mediated reductive amination reaction requires the reduced form of a coenzyme, such as NADH, and the NADH coenzyme is converted to the oxidized form as this reaction progresses. The quantity of coenzyme used can be substantially lowered by carrying out this reaction by having the amino acid dehydrogenase be present with an enzyme that has the ability to convert this oxidized form of the coenzyme to the reduced form (this ability is referred to hereinafter as the reduced coenzyme regenerating ability) and also with a compound that is a substrate for the enzyme.

The following, for example, can be used as polypeptides that have the reduced coenzyme regenerating ability: hydrogenases, formate dehydrogenases, alcohol dehydrogenases, aldehyde dehydrogenases, glucose-6-phosphate dehydrogenases, and glucose dehydrogenases.

A formate dehydrogenase is suitably used. A formate dehydrogenase of plant or microbial origin can be used as the formate dehydrogenase, while a formate dehydrogenase of microbial origin is preferred for industrial applications. Any microorganism capable of producing the enzyme can be used, and examples thereof include the following, which are known microorganisms capable of producing the enzyme: the genera *Candida, Kloeckera, Pichia, Lipomyces, Pseudomonas, Moraxella, Hyphomicrobium, Paracoccus, Thiobacillus*, and *Ancylobacter*.

An enzyme derived from a microorganism of the genus *Thiobacillus* or *Ancylobacter* is preferred. An enzyme derived from *Thiobacillus* sp. strain KNK65MA (FERM BP-7671) or *Ancylobacter aquaticus* strain KNK607M (FERM BP-7335) is more preferred.

As is well known, the production of a transformed microorganism is effective for obtaining a highly active microorganism that is a strong and efficient producer of formate dehydrogenase. In an example of a method for producing such a transformed microorganism, as described in WO 03/031626, the formate dehydrogenase gene from a strain that exhibits a formate dehydrogenase activity is cloned; a recombinant plasmid is then constructed using an appropriate vector; and this recombinant plasmid is used to transform an appropriate host microorganism. The recombinant DNA technology is well known in this field.

The thus obtained transformant that is a strong producer of formate dehydrogenase can be exemplified by *Escherichia coli* HB101 (pFT001) (FERN BP-7672) and *Escherichia coli* HB101 (pFT002) (FERM BP-7673), which are described in WO 03/031626 and contain the formate dehydrogenase gene from *Thiobacillus* sp. KNK65MA (FERM BP-7671), and by *Escherichia coli* HB101 (pFA001) (FERM BP-7334), which is described in WO 02/46427 and contains the formate dehydrogenase gene from *Ancylobacter aquaticus* strain KNK607M (FERM BP-7335).

The production of formate dehydrogenase by these transformants or by the previously referenced strains having a formate dehydrogenase activity may be carried out, for example, as described in WO 03/031626, by cultivation using an ordinary nutrient media; an enzyme induction treatment may also be carried out as necessary.

The amino acid dehydrogenase-mediated oxidative deamination reaction requires the oxidized form of a coenzyme, such as NAD, and the NAD coenzyme is converted to the reduced form as this reaction progresses. The quantity of coenzyme used can be substantially lowered by carrying out this reaction by having the amino acid dehydrogenase be present with an enzyme that has the ability to convert this reduced form of the coenzyme to the oxidized form (this ability is referred to hereinafter as the oxidized coenzyme regenerating ability) and also with a compound that is a substrate for the enzyme:

NADH oxidases, for example, can be used as polypeptides that have the oxidized coenzyme regenerating ability. NADH oxidases are preferred for the following reasons: they can utilize oxygen as the substrate for the coenzyme regenerating reaction; many NADH oxidases are specific for NADH; and the catalyzed reaction is irreversible. Two types of NADH oxidases are known, i.e., NADH oxidases that produce water (water-producing NADH oxidases) and NADH oxidases that produce hydrogen peroxide (hydrogen peroxide-producing NADH oxidases), and water-producing NADH oxidases are more preferred because hydrogen peroxide is known to have negative effects, for example, on enzymes.

Examples of enzyme sources for the water-producing NADH oxidases include enzymes originating from microorganisms selected from the group consisting of the genera *Streptococcus, Lactobacillus, Lactococcus, Leuconostoc, Enterococcus, Pediococcus, Methanococcus, Serpulina, Mycoplasma*, and *Giardia*. Enzymes originating from microorganisms of the genus *Streptococcus*, more preferably *Streptococcus mutans*, and even more preferably *Streptococcus mutans* NCIMB11723, are preferred. The amino acid sequence and the base sequence of the DNA encoding this amino acid sequence have already been reported for the water-producing NADH oxidase from *Streptococcus mutans* NCIMB11723 (Japanese Patent Application Laid-open No. H8-196281).

11. Catalase Addition

Catalase may be added to the aforementioned stereoinversion reaction. This reaction does proceed and a product can be obtained even when catalase is not added, but the substrate, reaction intermediate, or product may be degraded by hydrogen peroxide produced by the D-amino acid oxidase reaction and the yield may therefore be lowered. The addition of catalase inhibits this degradation of the substrate, reaction intermediate, or product and a better yield can therefore be expected. Catalase is an enzyme that catalyzes the decomposition of hydrogen peroxide into water and oxygen.

A catalase of animal, plant, or microbial origin can be used as this catalase, while a catalase of microbial origin is preferred for industrial applications. Any microorganism capable of producing the enzyme can be used, and examples thereof include the following, which are known microorganisms capable of producing the enzyme: the genera *Escherichia, Aspergillus, Micrococcus*, and *Rhodopseudomonas*.

Commercially available enzymes may also be used. Examples thereof include Catazyme 25L (Novozyme), Terminox Ultra 200L (Novozyme), and CATALASE (Beef Liver) (P-L Biochemicals, Inc.).

12. Transformant and the Like

The amino acid dehydrogenase, enzyme that has the coenzyme regenerating ability, D-amino acid oxidase, and catalase used in the present invention may be produced by preparing and culturing transformants into each of which the corresponding enzyme gene has been introduced or may be produced by preparing and culturing a transformant into which a plurality of the enzyme genes have been introduced.

In the present invention, the produced amino acid dehydrogenase, enzyme that has the coenzyme regenerating ability, D-amino acid oxidase, and catalase can in each case be used as it is or can be used in the form of a microorganism or a treated product of microorganism. This treated product of microorganism denotes, for example, a crude extract, freeze-dried cultured cells, acetone-dried cells, or disrupted cells thereof.

In addition, these enzymes may in each case be used in the form of the immobilized enzyme obtained by immobilizing the enzyme itself or the microbial cells as such using a known means. Immobilization can be carried out by, for example, a crosslinking method, covalent bonding method, physical adsorption method, or inclusion method, which are methods well known to those skilled in the art.

13. Production of L-Amino Acid and the Like

Production of a 2-oxo acid or D-amino acid by the oxidative deamination reaction, production of an L-amino acid by the reductive amination reaction, and production of an L-amino acid by the stereoinversion reaction according to the present invention can be carried out by the following processes.

The substrate for the oxidative deamination reaction is, for example, the L-amino acid of general formula (3) or the racemic amino acid of general formula (4). The substrate for the reductive amination reaction is, for example, the 2-oxo acid of general formula (2). The substrate for the stereoinversion reaction is, for example, the racemic amino acid of general formula (4) or the D-amino acid of general formula (5).

R in these substrates represents an optionally substituted $C_{1-20}$ alkyl group, an optionally substituted $C_{2-20}$ alkenyl group, an optionally substituted $C_{2-20}$ alkynyl group, an optionally substituted $C_{4-20}$ aryl group, or an optionally substituted $C_{5-20}$ aralkyl group.

The optionally substituted $C_{1-20}$ alkyl group for R is not particularly limited and can be exemplified by methyl, isopropyl, isobutyl, 1-methylpropyl, carbamoylmethyl, 2-carbamoylethyl, hydroxymethyl, 1-hydroxyethyl, mercaptomethyl, 2-methylthioethyl, (1-mercapto-1-methyl)ethyl, 4-aminobutyl, 3-guanidinopropyl, 4(5)-imidazolemethyl, ethyl, n-propyl, n-butyl, sec-butyl, tert-butyl, pentanyl, hexanyl, heptanyl, octanyl, 2,2-dimethylpropyl, chloromethyl, methoxymethyl, 2-hydroxyethyl, 3-aminopropyl, 2-cyanoethyl, 3-cyanopropyl, 4-(benzoylamino)butyl, or 2-methoxycarbonylethyl.

The optionally substituted $C_{2-20}$ alkenyl group is not particularly limited and can be exemplified by ethenyl, propenyl, butenyl, pentenyl, hexenyl, heptenyl, or octenyl.

The optionally substituted $C_{2-20}$ alkynyl group is not particularly limited and can be exemplified by ethynyl, propynyl, butynyl, pentynyl, hexynyl, heptynyl, or octynyl.

The optionally substituted $C_{5-20}$ aralkyl group is not particularly limited and can be exemplified by benzyl, indolylmethyl, thiazolemethyl, 4-hydroxybenzyl, naphthylmethyl, anthranylmethyl, pyridylmethyl, pyrimidylmethyl, indanylmethyl, indenylmethyl, phenylethyl, phenylpropyl, phenylbutyl, diphenylmethyl, 2-fluorobenzyl, 3-fluorobenzyl, 4-fluorobenzyl, or 3,4-methylenedioxybenzyl.

The optionally substituted $C_{4-20}$ aryl group can be exemplified by phenyl, 4-hydroxyphenyl, anthranyl, pyridyl, pyrimidyl, indanyl, indenyl, or naphthyl.

The substituent can be exemplified by amino, hydroxyl, nitro, cyano, carboxyl, alkyl, aralkyl, aryl, alkanoyl, alkenyl, alkynyl, alkoxyl, or halogen atom.

X represents a hydrogen atom, an alkali metal, or an alkaline-earth metal and is not particularly limited and examples thereof include a hydrogen atom, lithium, sodium, potassium, magnesium, and calcium.

14. Oxidative Deamination Reaction

The oxidative deamination reaction is run on the previously described substrate in an aqueous medium in the simultaneous presence of the previously described amino acid dehydrogenase, and the previously described enzyme that has the coenzyme regenerating ability and a compound that is a substrate for this enzyme. A coenzyme such as, for example, NAD may be added to this oxidative deamination reaction. Due to coenzymes, such as NAD, that are present in a microorganism, the reaction may proceed even without the addition of a coenzyme such as NAD; however, an improved reaction efficiency can be expected for the addition of a coenzyme such as NAD. The concentration of a coenzyme, such as NAD, added is preferably from at least 0 equivalent to not more than 2 equivalents, more preferably from at least 0.00001 equivalents to not more than 0.1 equivalents, and even more preferably from at least 0.0001 equivalents to not more than 0.01 equivalents, relative to the substrate.

15. Reductive Amination Reaction

The reductive amination reaction is run on the previously described substrate in an aqueous medium in the simultaneous presence of the previously described amino acid dehydrogenase, ammonia or a salt thereof, and the previously described enzyme that has the coenzyme regenerating ability and a compound that is a substrate for this enzyme. A coenzyme such as, for example, NAD may be added to this reductive amination reaction. Due to coenzymes, such as NAD, that are present in a microorganism, the reaction may proceed even without the addition of a coenzyme such as NAD; however, an improved reaction efficiency can be expected for the addition of a coenzyme such as NAD. The concentration of a coenzyme, such as NAD, added is preferably from at least 0 equivalent to not more than 2 equivalents, more preferably from at least 0.00001 equivalents to not more than 0.1 equivalents, and even more preferably from at least 0.0001 equivalents to not more than 0.01 equivalents, relative to the substrate.

16. Stereoinversion Reaction

The stereoinversion reaction is run on the previously described substrate in an aqueous medium in the simultaneous presence of the previously described D-amino acid oxidase, the previously described amino acid dehydrogenase, and the previously described enzyme that has the coenzyme regenerating ability and a compound that is a substrate for this enzyme. Catalase may also be added to this reaction. The addition of catalase serves to degrade hydrogen peroxide produced by the reaction of the D-amino acid oxidase and thus can inhibit degradation of the substrate, reaction intermediate, or product.

FAD may also be added to the reaction under consideration. FAD is a coenzyme for D-amino acid oxidase and its addition can be expected to improve the reaction efficiency. The concentration of FAD added is preferably from at least 0 equivalent to not more than 10 equivalents, more preferably from at least 0 equivalent to not more than 1 equivalent, and even more preferably from at least 0 equivalent to not more than 0.1 equivalents, relative to the substrate.

A coenzyme such as, for example, NAD may also be added to the stereoinversion reaction. Due to coenzymes, such as NAD, that are present in a microorganism, the reaction may proceed even without the addition of a coenzyme such as NAD; however, an improved reaction efficiency can be expected for the addition of a coenzyme such as NAD. The concentration of a coenzyme, such as NAD, added is preferably from at least 0 equivalent to not more than 2 equivalents, more preferably from at least 0.00001 equivalents to not more than 0.1 equivalents, and even more preferably from at least 0.0001 equivalents to not more than 0.01 equivalents, relative to the substrate.

Ammonia or a salt thereof may also be added to the stereoinversion reaction. The concentration of ammonia added is preferably from at least 0 equivalent to not more than 10 equivalents, more preferably from at least 0 equivalent to not more than 2 equivalents, and even more preferably from at least 0.1 equivalents to not more than 1.5 equivalents, relative to the substrate.

With regard to the concentration of the substrate charged in the oxidative deamination reaction, reductive amination reaction, and stereoinversion reaction, the reaction is run with the substrate dissolved or suspended at from at least 0.1% (w/v) to not more than 90% (w/v) and preferably from at least 1% (w/v) to not more than 60% (w/v). The reaction temperature for the oxidative deamination reaction, reductive amination reaction, and stereoinversion reaction is adjusted to an appropriate temperature from at least 10° C. to not more than 80° C. and preferably from at least 20° C. to not more than 60° C. Standing still or stirring may be carried out for some time while maintaining a pH of at least 4 but not more than 12 and preferably at least 6 but not more than 11. In addition, the substrate may be added all at once, or may be added in portions, or may be added continuously. The oxidative deamination reaction, reductive amination reaction, and stereoinversion reaction may each be run by a batch or continuous method.

The oxidative deamination reaction, reductive amination reaction, and stereoinversion reaction according to the present invention may each be carried out using, for example, an immobilized enzyme, a membrane reactor, and so forth. The aqueous medium may be water or a buffer or an aqueous medium comprising a water-soluble organic solvent, e.g., ethanol, with water or a buffer, or an appropriate solvent such as a two-layer system of an aqueous medium that contains an organic solvent that is poorly soluble in water, for example, an organic solvent such as ethyl acetate, butyl acetate, toluene, chloroform, n-hexane, and so forth. As necessary, for example, an antioxidant, surfactant, coenzyme, metal, and so forth, may also be added.

17. Isolation of Product

The produced L-amino acid, 2-oxo acid or D-amino acid can be isolated by separation and purification by a conventional separation method, for example, a separation method such as extraction, concentration, crystallization, or column chromatography, or by a combination of the preceding.

EXAMPLES

Specific examples of the present invention are given below. However, the present invention is not limited by these examples.

Example 1

Isolation and Purification of Amino Acid Dehydrogenase

*Rhodococcus qingshengii* strain KNK2108 was inoculated to 50 mL of a sterilized medium (1.0% beef extract, 1.0% polypeptone, 0.5% yeast extract, and 0.3% NaCl, pH 7.0 prior to sterilization) in a 500 mL Sakaguchi flask and aerobic shake cultivation was carried out for 23 hours at 30° C. 30 mL of the resulting culture fluid was inoculated to 3 L of a sterilized medium A (1.0% L-Phe, 0.1% polypeptone, 0.1% yeast extract, 0.1% beef extract, 0.45% $KH_2PO_4$, 0.62% $Na_2HPO_4$, 0.02% $MgSO_4.7H_2O$, 0.0002% $CaCl_2.2H_2O$, 0.00004% $ZnSO_4.7H_2O$, 0.00002% $FeCl_3.6H_2O$, and 0.01% ADEKA NOL LG 109, pH 7.0 prior to sterilization) in a 5 L jar fermenter and aerobic cultivation was performed for 31 hours at 30° C. with stirring at 450 rpm and an aeration rate of 0.3 vvm.

After the completion of cultivation, the cells were collected by centrifugal separation and were subsequently suspended in 0.1 M Tris (tris(hydroxymethyl)aminomethane)-HCl buffer (pH 8.0) that contained 10% glycerol and were disrupted with sonication and the disruptate was then centrifugally separated. The precipitate salted out by the addition of ammonium sulfate at 50% saturation to the supernatant was centrifugally separated and recovered. This fraction was dissolved in 0.1 M Tris (tris(hydroxymethyl)aminomethane)-HCl buffer (pH 8.0) that contained 20% glycerol, and was dialyzed using the same buffer and then applied to DEAE-TOYOPEARL (Tosoh Corporation) in order to carry out column chromatography; washing was carried out with the same buffer; elution was performed with the same buffer over a sodium chloride concentration gradient from 0 M to 0.4 M; and the active fraction was collected. This active fraction was applied to Blue Sepharose (GE Healthcare Biosciences) in order to carry out column chromatography and elution was performed using 0.1 M Tris (tris(hydroxymethyl)aminomethane)-HCl buffer (pH 8.0) that contained 20% glycerol over a sodium chloride concentration gradient from 0 M to 0.4 M. Ammonium sulfate was dissolved to a final concentration of 1 M in the obtained active fraction and column chromatography was performed using 6 mL RESOURCE PHE (GE Healthcare Biosciences) with elution using 0.1 M Tris (tris(hydroxymethyl)aminomethane)-HCl buffer (pH 8.0) that contained 20% glycerol over an ammonium sulfate concentration gradient from 1 M to 0 M. When the active fraction obtained in this manner was analyzed by SDS-polyacrylamide electrophoresis, the amino acid dehydrogenase was detected as a single band, thus confirming the purity of the purified enzyme.

Example 2

Properties of Amino Acid Dehydrogenase

The properties of the purified amino acid dehydrogenase obtained in Example 1 were examined as follows.

Specific Activity

The activity of the amino acid dehydrogenase was measured based on the rate of decline in the absorbance at a wavelength of 340 nm when 1.2 mL of 0.5 M $NH_3/NH_4Cl$ buffer (pH 9.0), 0.2 mL of 0.1 M sodium carbonate buffer (pH 9.0) that contained 3 mM NADH coenzyme, and 0.1 mL of the appropriately diluted enzyme solution were added to 1.5 mL of 0.1 M sodium carbonate buffer (pH 9.0) that contained 10 mM phenylpyruvic acid substrate and a reaction was carried out for 1 minute at 30° C. 1 unit is defined here as the quantity of enzyme that consumed 1 μmol NADH in 1 minute. The protein was quantified by the Bradford method using BSA as the reference protein. The purified amino acid dehydrogenase had a specific activity of 204 units/mg protein (30° C.).

Action Temperature Range and Optimal Temperature

The action temperature range and the optimal temperature were examined. The relative activity at individual temperatures is shown in FIG. 1 taking the activity at 30° C. to be 100%. This enzyme exhibited good activity in at least the investigated temperature range of 5 to 70° C., and the optimal temperature was 45° C. to 50° C.

Action pH Range and Optimal pH

Figure 2:
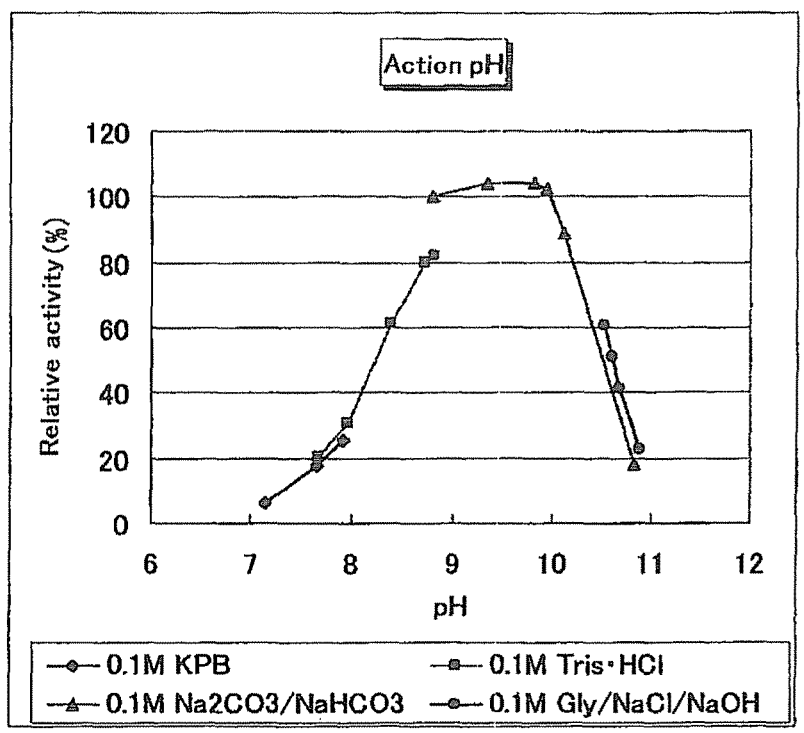
FIG. 2 is a graph that shows the relationship between the relative activity and the action pH (including the optimal pH) for an amino acid dehydrogenase according to an embodiment of the present invention.

The action pH range and the optimal pH were examined. The relative activity at individual pH values is shown in FIG. 2 taking the activity at pH 9.0 to be 100% and using 0.1 M potassium phosphate buffer for the pH range from 7.0 to 7.9, 0.1 M Tris-HCl buffer for the pH range from 7.9 to 8.8, 0.1 M sodium carbonate buffer for the pH range from 8.8 to 10.5, and 0.1 M glycine/sodium chloride/sodium hydroxide buffer for the pH range from 10.5 to 11.0. This enzyme was active in at least the investigated pH range of 7.1 to 11.0, and the optimal pH was 8.8 to 10.0.

Measurement of Molecular Weight

The purified amino acid dehydrogenase fraction obtained in Example 1 was concentrated using an ultrafiltration membrane (molecular weight cut off=10,000) and was then applied to Superdex 200HR 10/30 (GE Healthcare Biosciences) to carry out gel filtration chromatography by FPLC. Elution was performed using 0.1 M Tris (tris(hydroxymethyl)aminomethane)-HCl buffer (pH 8.0) that contained 20% glycerol and 0.15 M sodium chloride. Measurement of the molecular weight by comparison with the elution time of the reference protein provided approximately 94,000 (at least 86,000, but not more than 98,000). Measurement of the subunit molecular weight by comparison with the mobility of the reference protein in SDS-polyacrylamide electrophoresis gave approximately 46,000 (at least 43,000, but not more than 49,000), and the amino acid dehydrogenase of the present invention thus had a dimeric structure comprising identical subunits.

Substrate Specificity

The substrate specificity of the purified amino acid dehydrogenase was investigated. The enzyme activity was measured by using each substrate in place of the phenylpyruvic acid substrate in the procedure previously described for measuring the enzyme activity. In the case of the enzyme activity for naphthylpyruvic acid, 100 μL of the appropriately diluted enzyme solution was added to 100 μL of 0.1 M sodium carbonate buffer (pH 9.0) that contained 1.0 mg naphthylpyruvic acid, 12.3 mg ammonium sulfate, and 6.1 mg NADH and the increment in the 2-naphthylalanine produced in 30 minutes at 30° C. was determined by quantitation by HPLC. The HPLC analysis was run using the following: column: COSMOSIL 5C18-ARII (4.6 mm×250 mm, Nacalai Tesque, Inc.), eluent: 10 mM potassium phosphate buffer (pH 2.0)/acetonitrile=5/1, flow rate: 1.0 mL/min, column temperature: 40° C., detection: 210 nm. Here, 1 unit is defined as the quantity of enzyme that produces 1 μmol 2-naphthylalanine in 1 minute. In the case of the enzyme activity for indolepyruvic acid, 100 μL of the appropriately diluted enzyme solution was added to 100 μL of 0.1 M sodium carbonate buffer (pH 9.0) that contained 2.0 mg indolepyruvic acid, 26.0 mg ammonium sulfate, and 7.6 mg NADH and the increment in the L-tryptophan produced in 30 minutes at 30° C. was determined by quantitation by HPLC. The HPLC analysis was run using the following: column: CROWNPAK CR—(4.6 mm×150 mm, Daicel Chemical Industries, Ltd.), eluent: aqueous HClO$_4$ (pH 2.0), flow rate: 1.0 mL/min, column temperature: 30° C., detection: 210 nm. Here, 1 unit is defined as the quantity of enzyme that produces 1 μmol L-tryptophan in 1 minute. The relative activity values, assigning 100% to the activity for phenylpyruvic acid, are shown in Table 1.

TABLE 1

| Substrate | Relative activity (%) |
| --- | --- |
| Phenylpyruvic acid | 100.0 |
| 4-Hydroxyphenylpyruvic acid | 96.3 |
| Naphthylpyruvic acid | 38.8 |
| Indolepyruvic acid | 19.7 |
| Homophenylpyruvic acid | 19.1 |
| 2-Oxo-4-(methylthio)butanoic acid | 34.6 |
| 2-Oxo-4-methylvaleric acid | 3.5 |

Example 3

Determination of N-Terminal Amino Acid Sequence and Internal Amino Acid Sequence of Amino Acid Dehydrogenase The purified amino acid dehydrogenase obtained in Example 1 was preparatively purified by reversed-phase HPLC (column: YMC-Pack PROTEIN-RP from YMC Co., Ltd., eluent: 20% aqueous acetonitrile to 80% aqueous acetonitrile gradient, flow rate: 1 mL/min, column temperature: 25° C., detection: 230 nm) and the N-terminal amino acid sequence was then determined using a gas-phase protein sequencer PPSQ-33A (Shimadzu). In addition, the purified amino acid dehydrogenase of Example 1 was subjected to the action of V8 protease (Wako Pure Chemical Industries, Ltd.) in the presence of 4 M urea; the produced polypeptide fragments were purified using the same reversed-phase HPLC as above; and an internal amino acid sequence was determined for the amino acid dehydrogenase by the same method as described above.

Example 4

Isolation Of Amino Acid Dehydrogenase Gene

*Rhodococcus qingshengii* strain KNK2108 was inoculated to 5 mL of a sterilized medium (1.0% beef extract, 1.0% polypeptone, 0.5% yeast extract, and 0.3% NaCl, pH 7.0 prior to sterilization) in a test tube and aerobic shake cultivation was carried out for 38 hours at 30° C. The chromosomal DNA was obtained from the resulting cells using an UltraClean Microbial DNA Isolation Kit (from MO BIO Laboratories, Inc.). Using a DNA primer designed based on the N-terminal amino acid sequence (Primer-1: SEQ ID NO:3 in Sequence Listing) and a DNA primer designed based on the internal amino acid sequence (Primer-2: SEQ ID NO:4 in Sequence Listing), PCR was run on the already acquired chromosomal DNA as a template. This PCR was carried out as follows: 0.25 μL Ex Taq DNA Polymerase (Takara Bio Inc.), 5 μL 10× Ex Taq Buffer (Takara Bio Inc.), 4 μL of each 2.5 mM dNTP solution, and 2 μL of a 20 μM aqueous solution of each primer were added to 100 ng template DNA; sufficient sterilized water was then added to prepare a reaction mixture adjusted to a total volume of 50 μL; 30 cycles of heat denaturation (94° C., 60 seconds), annealing (48° C., 60 seconds), and elongation reaction (72° C., 60 seconds) were repeated; and cooling to 4° C. was then carried out. The result was the acquisition of a part (designated the partial gene) of the target amino acid dehydrogenase gene. The base sequence of this partial gene was determined using a 3130xl Genetic Analyzer DNA sequencer (Applied Biosystems).

The following procedure was carried out in order to acquire the full length of the target gene. Based on the base sequences in the partial gene corresponding to the N-terminal side region and the C-terminal side region of the enzyme, DNA primers directed to outside the partial gene were synthesized (Primer-3: SEQ ID NO:5 in Sequence Listing, Primer-4: SEQ ID NO:6 in Sequence Listing). These primers were used to carry out inverse PCR with a template DNA obtained by digesting the previously obtained chromosomal DNA with the BamHI or HincII restriction enzyme followed by cyclization using T4 DNA ligase. This PCR was run substantially as described above, but using heat denaturation (96° C., 30 seconds), annealing (60° C., 60 seconds), elongation reaction (72° C., 300 seconds).

As a result, a DNA fragment was obtained that contained the gene regions further outside the already acquired partial gene. The base sequence of this DNA fragment was determined by the same method previously described. By combination of this base sequence with the existing base sequence of the partial gene, the full base sequence of the amino acid dehydrogenase gene, shown in SEQ ID NO:7 of the Sequence Listing, from the start codon to the stop codon was determined. The thus determined full base sequence was confirmed to contain bases coding for the N-terminal amino acid sequence and internal amino acid sequence which were determined in Example 3 using the purified amino acid dehydrogenase. Then, using primers that had sequences in which the cleavage sites for the EcoRI and KpnI restriction enzymes were ligated, respectively, at the N-terminal region and C-terminal region of the amino acid dehydrogenase gene (Primer-5: SEQ ID NO:8 in Sequence Listing, Primer-6: SEQ ID NO:9 in Sequence Listing), the DNA between them was amplified by PCR using the previously obtained chromosomal DNA as a template, thereby obtaining the open reading frame DNA fragment shown in Sequence Listing SEQ ID NO:2. This PCR was carried out as follows: 0.5 μL PrimeSTAR DNA Polymerase (Takara Bio Inc.), 10 μL 5× PrimeSTAR Buffer (Takara Bio Inc.), 4 μL of each 2.5 mM dNTP solution, and 0.5 μL of a 20 μM aqueous solution of each primer were added to 100 ng template DNA; sufficient sterilized water was then added to prepare a reaction mixture adjusted to a total volume of 50 μL; 25 cycles of heat denaturation (98° C., 10 seconds), annealing (55° C., 5 seconds), and elongation reaction (72° C., 90 seconds) were repeated; and cooling to 4° C. was then carried out.

Example 5

Figure 3:
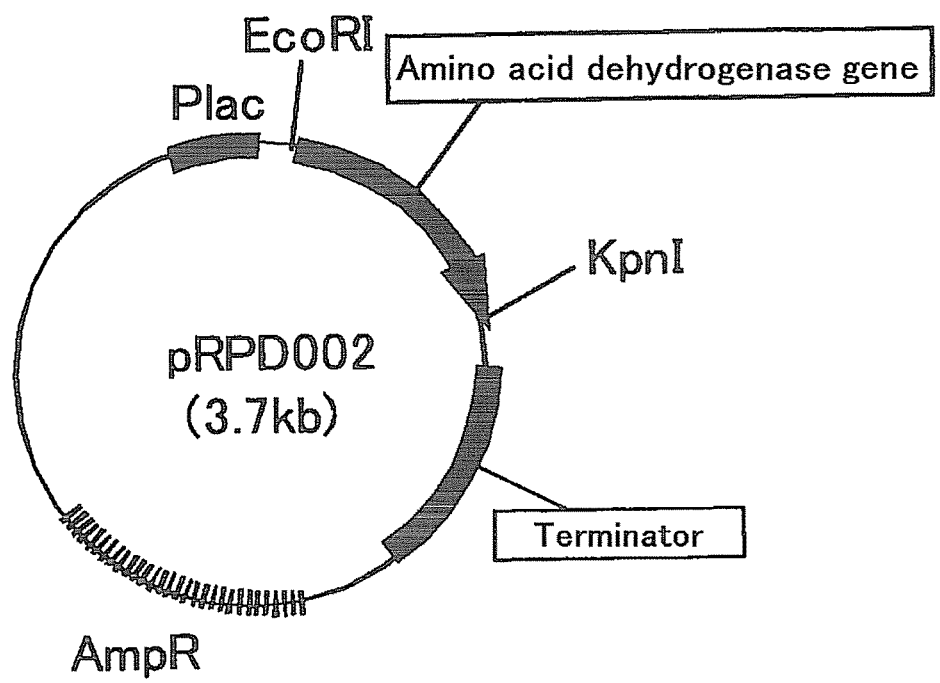
FIG. 3 is a diagram that shows the components of recombinant plasmid pRPD002, which incorporates an amino acid dehydrogenase gene according to an embodiment of the present invention.

Construction of Recombinant Plasmid that Expresses Amino Acid Dehydrogenase Gene The DNA fragment obtained in Example 4 was digested with the restriction enzymes EcoRI and KpnI followed by ligation using T4 DNA ligase with the vector plasmid pUCT (a plasmid vector obtained by the destruction of the NdeI site of pUCNT (refer to WO 94/03613)) that had been digested with the same enzymes to obtain the plasmid pRPD002 shown by the restriction enzyme map in FIG. 3 and designed to be capable of strong expression of the amino acid dehydrogenase gene.

Example 6

Construction of Transformant Using Recombinant DNA Containing Amino Acid Dehydrogenase Gene Transformation was performed by mixing the pRPD002 plasmid obtained in Example 5 with competent cells of Escherichia coli HB101. The subsequent plating on a culture medium (10 g tryptone, 5 g yeast extract, 10 g sodium chloride, 15 g agar, and 100 mg ampicillin, made to 1 L with deionized water; pH 7.0 before sterilization; the ampicillin was added after sterilization) yielded colonies of the transformant Escherichia coli HB101 (pRPD002), which contained recombinant DNA containing the amino acid dehydrogenase gene.

Colonies of the obtained transformant were inoculated to 6 mL of a sterilized culture medium (16 g tryptone, 10 g yeast extract, 5 g sodium chloride, and 100 mg ampicillin, made to 1 L with deionized water; pH 7.0 before sterilization; the ampicillin was added after sterilization) in a test tube, followed by aerobic cultivation with shaking for 24 hours at 37° C. The cells were collected from the obtained culture by centrifugation and were suspended in 0.1 M Tris-HCl buffer (pH 8.0). After disruption of the cells with sonication, the insoluble material from the cells was removed by centrifugal separation to obtain a solution of the transformant-derived amino acid dehydrogenase. An amino acid dehydrogenase activity was confirmed when the amino acid dehydrogenase activity of the obtained enzyme solution was measured using the method described in Example 2.

Example 7

L-Amino Acid Synthesis by Reductive Amination Using Cells with Amino Acid Dehydrogenase Activity Rhodococcus qingshengii KNK2108 was inoculated to 6 mL of a sterilized medium A as described in Example 1, in a test tube and was aerobically shake cultured for 48 hours at 30° C. The cells in a 5 mL portion of the obtained centrifugation collected by centrifugal separation and suspended in 1.0 mL of 0.1 M Tris-HCl buffer (pH 8.0). After disruption of the cells by sonication, centrifugation was carried out and the supernatant was recovered as a crude enzyme solution. 150 μL of the obtained crude enzyme solution, 1.5 mg naphthylpyruvic acid, 1.9 mg ammonium sulfate, 9.5 mg NADH, and 150 μl. of 0.1 M Tris-HCl buffer (pH 8.0) were mixed; a reaction was run for 16 hours at 30° C.; the reaction solution was then diluted 50-fold with water; and the supernatant afforded by centrifugation was analyzed by HPLC to quantitate L-naphthylalanine.

The HPLC analysis was run using the following conditions: column: CHIROBIOTIC T (4.6 mm×250 mm, ASTEC), eluent: water/ethanol 3/7, flow rate: 0.6 mL/min, column temperature: 40° C., detection: 210 nm. The results showed the production of L-naphthylalanine in a reaction yield of 54.6 mol.

Example 8

L-Amino Acid Synthesis Using Transformant

The cells were collected by centrifugal separation from the culture obtained in Example 6 of the transformant Escherichia coli HB101 (pRPD002), which had an amino acid dehydrogenase activity. The cells were suspended in 0.1 M Tris-HCl buffer (pH 8.0) and were disrupted by sonication to prepare a disrupted cell solution. In addition, the cells were collected by centrifugation from the culture of a transformant that had a formate dehydrogenase activity (prepared by the method described below) and were suspended in 0.1 M Tris-HCl buffer (pH 8.0) and disrupted with sonication to prepare a disrupted cell solution. In addition, the cells were collected by centrifugation from the culture of a transformant that had a D-amino acid oxidase activity (prepared by the method described below) and were suspended in 0.1 M Tris-HCl buffer (pH 8.0) and disrupted with sonication to prepare a disrupted cell solution. These disrupted cell solutions were reacted with DL-naphthylalanine, DL-homophenylalanine, or DL-tryptophan to synthesize the corresponding L-amino acid by a stereoinversion reaction.

The following procedure was used to obtain the culture of a transformant that had a formate dehydrogenase activity. *Escherichia coli* HB101 (pFT002) (FERM BP-7673), a transformant having a formate dehydrogenase activity originating from *Thiobacillus* sp. KNK65MA (FERM BP-7671), was inoculated to 6 mL of a sterilized culture medium (16 g tryptone, 10 g yeast extract, 5 g sodium chloride, 1 L water, pH 7.0 before sterilization) in a test tube and shake cultivation was carried out for 24 hours at 30° C. The following procedure was used to obtain the culture of a transformant that had a D-amino acid oxidase activity. *Escherichia coli* HB101 (pCDA003) (FERM BP-10639), a transformant having a D-amino acid oxidase activity originating from *Candida intermedia* NBRC0761, was inoculated to 6 mL of a sterilized culture medium (16 g tryptone, 10 g yeast extract, 5 g sodium chloride, 1 L water, pH 7.0 before sterilization) in a test tube and shake cultivation was carried out for 24 hours at 37° C.

(8-1) Synthesis of L-naphthylalanine from DL-naphthylalanine

The cells were collected by centrifugation from a 10 mL portion of the culture of the previously described transformant *Escherichia coli* HB101 (pRPD002), which had an amino acid dehydrogenase activity, from a 10 mL portion of the culture of the previously described transformant that had a D-amino acid oxidase activity, and from a 10 mL portion of the culture of the previously described transformant that had a formate dehydrogenase activity. In each case the cells were suspended in 1 mL 0.1 M Tris-HCl buffer (pH 8.0) and disrupted with sonication to prepare a disrupted cell solution. The obtained disrupted cell solutions were mixed with 10 mg DL-naphthylalanine, 2 µL catalase (Catazyme 25L, Novozyme), 0.37 mg NAD, 27 mg ammonium formate, and 0.1 M Tris-HCl buffer (pH 8.0) to prepare a 1.0 mL reaction mixture, and a reaction was run for 19 hours at 30° C. The reaction was diluted 20-fold with water and the centrifugal supernatant was analyzed by HPLC to quantitate the amino acid. This quantitation of the amino acid by HPLC analysis was performed using the same conditions as in Example 7. According to the results, L-naphthylalanine with an optical purity of 100% e.e. was obtained at a reaction yield of 97.0 mol % based on the racemic amino acid.

(8-2) Synthesis of L-homophenylalanine from DL-homophenylalanine

Disrupted cell solutions prepared as described above in Example (8-1) were mixed with 10 mg DL-homophenylalanine, 2 µL catalase (Catazyme 25L, Novozyme), 0.37 mg NAD$^+$, 27 mg ammonium formate, and 0.1 M Tris-HCl buffer (pH 8.0) to prepare a 1.0 mL reaction mixture, and a reaction was run for 19 hours at 30° C. The reaction was diluted 20-fold with water and the centrifugal supernatant was analyzed by HPLC to quantitate the amino acid. This quantitation of the amino acid by HPLC analysis was performed using the same conditions as in Example 7. According to the results, L-homophenylalanine with an optical purity of 100% e.e. was obtained at a reaction yield of 98.6 mol % based on the racemic amino acid.

(8-3) Synthesis of L-tryptophan from DL-tryptophan

Disrupted cell solutions prepared as described above in Example (8-1) were mixed with 10 mg DL-tryptophan, 2 µL catalase (Catazyme 25L, Novozyme), 0.37 mg NAD$^+$, 27 mg ammonium formate, and 0.1 M Tris-HCl buffer (pH 8.0) to prepare a 1.0 mL reaction mixture, and a reaction was run for 19 hours at 30° C. The reaction was diluted 20-fold with water and the centrifugal supernatant was analyzed by HPLC to quantitate the amino acid. This quantitation of the amino acid by HPLC analysis was performed using the same conditions as in Example 7. According to the results, L-tryptophan with an optical purity of 100% e.e. was obtained at a reaction yield of 94.5 mol % based on the racemic amino acid.

Example 9

Construction of Transformant Using Recombinant DNA Containing Amino Acid Dehydrogenase Gene and Recombinant DNA Containing Chaperone Gene Transformation was performed by mixing competent cells of *Escherichia coli* HB101 with the pRPD002 plasmid obtained in Example 5 and the commercially available chaperone plasmid pGrO7 (Chaperone Plasmid Set from Takara Bio Inc.) to construct the transformant *Escherichia coli* HB101 (pRPD002, pGrO7), which had the ability to express the amino acid dehydrogenase gene and a chaperone gene.

Example 10

Production of Amino Acid Dehydrogenase Using Transformant

The *Escherichia coli* HB101 (pRPD002, pGrO7) transformant obtained in Example 9 was inoculated to 6 mL of a sterilized culture medium (16 g tryptone, 10 g yeast extract, 5 g sodium chloride, 100 mg ampicillin, and 100 mg chloramphenicol, made to 1 L with deionized water; pH 7.0 before sterilization; the ampicillin and chloramphenicol were added after sterilization) in a test tube, followed by aerobic cultivation with shaking for 24 hours at 30° C. The cells were collected from 1 mL of the obtained culture by centrifugation and were suspended in 1 mL 0.1 M Tris-HCl buffer (pH 8.0). After disruption of the cells with sonication, the insoluble material from the cells was removed by centrifugation separation to obtain a cell free extract of the transformant extract (soluble fraction). The insoluble material from the cells was resuspended in 1 mL of 0.1 M Tris-HCl buffer (pH 8.0) to prepare an insoluble fraction solution. A cell free extract (soluble fraction) and an insoluble fraction solution of the transformant were also prepared by the same methods as described above (with the exception that the chloramphenicol was not added to the culture medium) from the *Escherichia coli* HB101 (pRPD002) transformant obtained in Example 6.

The soluble fraction and insoluble fraction from each of the transformants were analyzed by SDS-polyacrylamide gel electrophoresis. For the *Escherichia coli* HB101 (pRPD002) transformant, the majority of the amino acid dehydrogenase was found to be present in the insoluble fraction, but for the *Escherichia coli* HB101 (pRPD002, pGrO7) transformant, the majority of the amino acid dehydrogenase was found to be present in the soluble fraction.

The amino acid dehydrogenase activity was measured by the method described in Example 2 on the cell free extracts obtained from both transformants. The cell free extract obtained from the *Escherichia coli* HB101 (pRPD002, pGrO7) transformant exhibited an amino acid dehydrogenase activity that was approximately 61 times that of the cell free extract obtained from the *Escherichia coli* HB101 (pRPD002) transformant.

Example 11

Construction of Transformant Transformed with Vector Containing Amino Acid Dehydrogenase Gene and Formate Dehydrogenase Gene Carrying out PCR using PrimeSTAR DNA Polymerase (Takara Shuzo Co., Ltd), a gene was obtained in which the NdeI recognition site was added at the 5' terminal side and the EcoRI recognition site was added at the 3' terminal side of the amino acid dehydrogenase gene (SEQ ID NO:2) from *Rhodococcus qingshengii* KNK2108 (FERM BP-11067). The recombinant vector pNRH was constructed by inserting the DNA fragment yielded by this PCR between the NdeI recognition site and the EcoRI recognition site, which were downstream from the lac promoter in the plasmid pUCN18 (a plasmid provided by the destruction of the NdeI site of pUC18 (Takara Bio Inc., GenBank Accession No. L09136) by changing the T at position 185 to A by PCR and the introduction of a new NdeI site by changing the GC at positions 471 to 472 to TG). Using the thereby constructed recombinant vector pNRH, competent cells of *Escherichia coli* HB101 (Takara Bio Inc.) were transformed to obtain *Escherichia coli* HB101 (pNRH). The resulting transformant was inoculated to 6 mL of a sterilized culture medium (16 g tryptone, 10 g yeast extract, 5 g sodium chloride, and 100 mg ampicillin, made to 1 L with deionized water; pH 7.0 before sterilization; the ampicillin was added after sterilization) in a test tube and aerobic cultivation with shaking was carried out for 24 hours at 30° C. The cells were collected from the resulting culture by centrifugation and the pNRH plasmid was extracted using a QIAprep Spin Miniprep Kit (QIAGEN).

Then, carrying out PCR using PrimeSTAR DNA Polymerase (Takara Shuzo Co., Ltd), a gene was obtained in which the EcoRI recognition site was added at the 5' terminal side and the KpnI recognition site was added at the 3' terminal side of the formate dehydrogenase gene (refer to Sequence Listing SEQ ID NO:3 in WO 03/031626) from *Thiobacillus* sp. KNK65MA (FERM BP-7671). The recombinant vector pNRHSFD was constructed by inserting the resulting DNA fragment between the EcoRI recognition site and the KpnI recognition site of the pNRH plasmid constructed as described above. Competent cells of *Escherichia coli* HB101 (Takara Bio Inc.) were transformed using the recombinant vector pNRHSFD to obtain the transformant *Escherichia coli* HB101 (pNRHSFD), which had an amino acid dehydrogenase activity and a formate dehydrogenase activity.

Example 12

Synthesis of L-Naphthylalanine Using Transformant Transformed with Vector Containing Amino Acid Dehydrogenase Gene and Formate Dehydrogenase Gene The *Escherichia coli* HB101 (pNRHSFD) transformant obtained in Example 11 was inoculated to 6 mL of a sterilized culture medium (16 g tryptone, 10 g yeast extract, 5 g sodium chloride, and 100 mg ampicillin, made to 1 L with deionized water; pH 7.0 before sterilization; the ampicillin was added after sterilization) in a test tube and aerobic shake cultivation was carried out for 24 hours at 30° C. The cells were collected by centrifugal separation from the resulting culture and were suspended in 0.1 M Tris-HCl buffer (pH 8.0) and disrupted with sonication to prepare a disrupted cell solution. A disrupted cell solution of a transformant that had a D-amino acid oxidase activity was produced by the same method as described in Example 8. The obtained disrupted cell solutions were mixed with 10 mg DL-naphthylalanine, 2 µL. catalase (Catazyme 25L, Novozyme), 0.37 mg NAD, 27 mg ammonium formate, and 0.1 M Tris-HCl buffer (pH 8.0) to prepare a 1.0 mL reaction mixture, and a reaction was run for 19 hours at 30° C. The reaction was diluted 20-fold with water and the centrifugal supernatant was analyzed by HPLC to quantitate the amino acid. This quantitation of the amino acid by HPLC analysis was performed using the same conditions as in Example 7. According to the results, L-naphthylalanine with an optical purity of 100% e.e. was obtained at a reaction yield of 94.2 mol % based on the racemic amino acid.

Example 13

Construction of Transformant Transformed with Vector Containing Amino Acid Dehydrogenase Gene, Formate Dehydrogenase Gene, and D-Amino Acid Oxidase Gene Carrying out PCR using PrimeSTAR DNA Polymerase (Takara Shuzo Co., Ltd), a gene was obtained in which the KpnI recognition site was added at the 5' terminal side and the BamHI recognition site was added at the 3' terminal side of the D-amino acid oxidase gene (refer to Sequence Listing SEQ ID NO:2 in WO 07/015511) from *Candida intermedia* strain NBRC0761. The recombinant vector pNRHSFDCDA was constructed by inserting the resulting DNA fragment between the KpnI recognition site and the BamHI recognition site of the pNRHSFD plasmid constructed in Example 11. Competent cells of *Escherichia coli* HB101 (Takara Bio Inc.) were transformed using the recombinant vector pNRHSFD-CDA to obtain the transformant *Escherichia coli* HB101 (pNRHSFDCDA), which had an amino acid dehydrogenase activity, a formate dehydrogenase activity, and a D-amino acid oxidase activity.

Example 14

L-Amino Acid Synthesis Using Transformant Transformed with Vector Containing Amino Acid Dehydrogenase Gene, Formate Dehydroqenase Gene, and D-Amino Acid Oxidase Gene (14-1) Synthesis of L-Naphthylalanine from DL-Naphthylalanine The *Escherichia coli* HB101 (pNRHSFDCDA) transformant obtained in Example 13, which had an amino acid dehydrogenase activity, a formate dehydrogenase activity, and a D-amino acid oxidase activity, was inoculated to 6 mL of a sterilized culture medium (16 g tryptone, 10 g yeast extract, 5 g sodium chloride, and 100 mg ampicillin, made to 1 L with deionized water; pH 7.0 before sterilization; the ampicillin was added after sterilization) in a test tube and aerobic shake cultivation was carried out for 24 hours at 30° C. The cells were collected by centrifugal separation from 10 mL of the resulting culture and were suspended in 1 mL of 0.1 M Tris-HCl buffer (pH 8.0) to prepare a cell concentrate. The resulting cell concentrate was mixed with 10 mg DL-naphthylalanine, 2 µL catalase (Catazyme 25L, Novozyme), 0.37 mg NAD, 27 mg ammonium formate, and 0.1 M Tris-HCl buffer (pH 8.0) to prepare a 1.0 mL reaction mixture, and a reaction was run for 24 hours at 30° C. The reaction was diluted 20-fold with water and the centrifugal supernatant was analyzed by HPLC to quantitate the amino acid. This quantitation of the amino acid by HPLC analysis was performed using the same conditions as in Example 7. According to the results, L-naphthylalanine with an optical purity of 95.9% e.e. was obtained at a reaction yield of 89.6 mol % based on the racemic amino acid.

(14-2) Synthesis of L-homophenylalanine from DL-homophenylalanine

A cell concentrate prepared as described above in Example (14-1) was mixed with 10 mg DL-homophenylalanine, 2 μL catalase (Catazyme 25L, Novozyme), 0.37 mg NAD⁺, 27 mg ammonium formate, and 0.1 M Tris-HCl buffer (pH 8.0) to prepare a 1.0 mL reaction mixture, and a reaction was run for 24 hours at 30° C. The reaction was diluted 20-fold with water and the centrifugal supernatant was analyzed by HPLC to quantitate the amino acid. This quantitation of the amino acid by HPLC analysis was performed using the same conditions as in Example 7. According to the results, L-homophenylalanine with an optical purity of 100% e.e. was obtained at a reaction yield of 102.7 mol % based on the racemic amino acid.

(14-3) Synthesis of L-tryptophan from DL-tryptophan

A cell concentrate prepared as described above in Example (14-1) was mixed with 10 mg DL-tryptophan, 2 μL catalase (Catazyme 25L, Novozyme), 0.37 mg NAD⁺, 27 mg ammonium formate, and 0.1 M Tris-HCl buffer (pH 8.0) to prepare a 1.0 mL reaction mixture, and a reaction was run for 24 hours at 30° C. The reaction was diluted 20-fold with water and the centrifugal supernatant was analyzed by HPLC to quantitate the amino acid. This quantitation of the amino acid by HPLC analysis was performed using the same conditions as in Example 7. According to the results, L-tryptophan with an optical purity of 100% e.e. was obtained at a reaction yield of 97.3 mol % based on the racemic amino acid.

What is claimed is:

1. A recombinant plasmid obtained by inserting a DNA into a vector,
   wherein the DNA is an isolated DNA according to any of the following (a), (b), (c), (d), (e) and (f):
   (a) a DNA encoding a polypeptide comprising the amino acid sequence shown in Sequence Listing SEQ ID NO:1;
   (b) a DNA encoding a polypeptide that has an amino acid dehydrogenase activity and comprises an amino acid sequence provided by the substitution, insertion, deletion and/or addition of not more than 25 amino acids in the amino acid sequence shown in Sequence Listing SEQ ID NO:1;
   (c) a DNA encoding polypeptide that has an amino acid dehydrogenase activity and comprises an amino acid sequence that has at least 90% sequence identity with the amino acid sequence shown in Sequence Listing SEQ ID NO:1;
   (d) a DNA comprising the base sequence shown in Sequence Listing SEQ ID NO:2;
   (e) a DNA that encodes a polypeptide having an amino acid dehydrogenase activity and has a base sequence provided by the substitution, insertion, deletion and/or addition of not more than 50 bases in the base sequence shown in Sequence Listing SEQ ID NO:2; and
   (f) a DNA that encodes a polypeptide having an amino acid dehydrogenase activity and comprises a base sequence that has at least 90% sequence identity with the base sequence shown in Sequence Listing SEQ ID NO:2.

2. A transformant obtained by transforming a host microorganism with the recombinant plasmid according to claim 1.

3. A transformant obtained by transforming a host microorganism with a DNA according to any of the following (a), (b), (c), (d), (e) and (f):
   (a) a DNA encoding a polypeptide comprising the amino acid sequence shown in Sequence Listing SEQ ID NO:1;
   (b) a DNA encoding a polypeptide that has an amino acid dehydrogenase activity and comprises an amino acid sequence provided by the substitution, insertion, deletion and/or addition of not more than 25 amino acids in the amino acid sequence shown in Sequence Listing SEQ ID NO:1;
   (c) a DNA encoding polypeptide that has an amino acid dehydrogenase activity and comprises an amino acid sequence that has at least 90% sequence identity with the amino acid sequence shown in Sequence Listing SEQ ID NO:1;
   (d) a DNA comprising the base sequence shown in Sequence Listing SEQ ID NO:2;
   (e) a DNA that encodes a polypeptide having an amino acid dehydrogenase activity and has a base sequence provided by the substitution, insertion, deletion and/or addition of not more than 50 bases in the base sequence shown in Sequence Listing SEQ ID NO:2; and (f) a DNA that encodes a polypeptide having an amino acid dehydrogenase activity and comprises a base sequence that has at least 90% sequence identity with the base sequence shown in Sequence Listing SEQ ID NO:2, and a DNA encoooding a chaperone.

4. The transformant according to claim 2 or 3, wherein the host microorganism is *Escherichia coli*.

5. A process for producing an amino acid dehydrogenase, comprising:
    culturing a microorganism capable of producing a polypeptide;
    accumulating the polypeptide in the culture; and
    recovering the polypeptide,
    wherein the polypeptide is a polypeptide according to any of the following (g), (h) and (i):
    (g) a polypeptide comprising the amino acid sequence shown in Sequence Listing SEQ ID No. 1;
    (h) a polypeptide that has an amino acid dehydrogenase activity and comprises an amino acid sequence provided by the substitution, insertion, deletion and/or addition of not more than 25 amino acids in the amino acid sequence shown in Sequence Listing SEQ ID No. 1;
    (i) a polypeptide that has an amino acid dehydrogenase activity and comprises an amino acid sequence that has at least 90% sequence identity with the amino acid sequence shown in Sequence Listing SEQ ID No. 1,
    wherein the polypeptide exhibits activity for a 2-oxo acid represented by general formula (1):

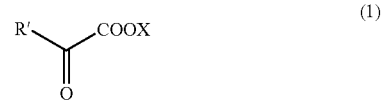

wherein R' represents an optionally substituted $C_{5-20}$ alkyl group, an optionally substituted $C_{5-20}$ alkenyl group, an optionally substituted $C_{5-20}$ alkynyl group, an optionally substituted $C_{4-20}$ aryl group, or an optionally substituted $C_{5-20}$ aralkyl group, and X represents a hydrogen atom, an alkali metal, or an alkaline-earth metal; and exhibits an activity for naphthylpyruvic acid that is at least one-fiftieth of an activity thereof for phenylpyruvic acid.

6. The process for producing an amino acid dehydrogenase according to claim 5, wherein the microorganism is the transformant according to claim 2 or 3.

* * * * *

SEQUENCE LISTING

```
<160> NUMBER OF SEQ ID NOS: 9

<210> SEQ ID NO 1
<211> LENGTH: 368
<212> TYPE: PRT
<213> ORGANISM: Rhodococcus qingshengii

<400> SEQUENCE: 1

Met Ser Ile Asp Asp Glu Leu Arg Trp Asp Gly Glu Leu Thr Val Thr
1               5                   10                  15

Arg His Asp Arg Glu Thr Gly Thr Thr Phe Val Ile Arg Ile Asp Ser
                20                  25                  30

Thr Arg Leu Gly Pro Ala Ser Gly Gly Thr Arg Ala Ala His Tyr Pro
            35                  40                  45

Ser Ile Gly His Ala Leu Ala Asp Ala Gly Lys Leu Ala Gly Ala Met
        50                  55                  60

Thr Leu Lys Met Ala Val Ser Asp Leu Pro Met Gly Gly Gly Lys Ser
65                  70                  75                  80

Val Ile Ala Leu Pro Ala Pro Arg Asn Gln Ile Asp Ala Ala Thr Trp
                85                  90                  95

Ser Arg Ile Leu Gly Ile His Ala Glu Asn Ile Asp Lys Leu Glu Gly
                100                 105                 110

Asn Tyr Trp Thr Gly Pro Asp Val Asn Thr Asn Ser Ser Asp Met Asp
            115                 120                 125

Gln Leu Ser Arg Thr Thr Arg Tyr Val Phe Gly Arg Ser Val Asp Lys
        130                 135                 140

Gly Gly Ala Gly Ser Ser Ala His Ala Thr Ala Leu Gly Val Phe Glu
145                 150                 155                 160

Ala Met Lys Ala Thr Ala Arg Arg Gly Leu Gly Thr Leu Asp Gly
                165                 170                 175

Arg Thr Val Leu Val Gln Gly Leu Gly Ala Val Gly Gly Asp Val Val
            180                 185                 190

Arg Leu Ala Ala Gln Ala Gly Ala Arg Leu Leu Val Ala Asp Thr Asp
        195                 200                 205

Pro Gln Arg Leu Glu Ala Ala Ser Leu Ala Gly His Thr Val Val Pro
    210                 215                 220
```

```
Ala Gly Glu Val Leu Arg Thr Pro Cys Asp Leu Phe Ala Pro Cys Ala
225                 230                 235                 240

Met Gly Gly Ile Ile Asp Phe Ala Ala Ala Ala Ser Ile Pro Thr Leu
            245                 250                 255

Ala Val Ala Gly Ala Ala Asn Asn Ile Leu Thr Asp Ala Ala Ala Gly
        260                 265                 270

Glu Val Leu Arg Asp Arg Gly Val Leu Cys Ala Pro Asp Phe Val Ala
    275                 280                 285

Asn Ala Gly Gly Ala Phe His Leu Val Gly Arg Glu Val Leu Gly Trp
        290                 295                 300

Asn Glu Asp Tyr Val Val Glu Arg Thr Arg Gly Ile Gly Arg Thr Leu
305                 310                 315                 320

Asp Glu Val Tyr Ser Leu Ser Glu Glu Arg Gly Ile Thr Thr Glu Ala
                325                 330                 335

Ala Ala Leu Met Leu Ala Arg Ala Arg Leu Ser Pro Ala Ser Thr Ala
            340                 345                 350

Ala Ala Ala Thr Ser Ala Ala Pro Ala Ala Ala Ala Ser Pro Ala
            355                 360                 365
```

<210> SEQ ID NO 2
<211> LENGTH: 1107
<212> TYPE: DNA
<213> ORGANISM: Rhodococcus qingshengii

<400> SEQUENCE: 2

```
atgagtatcg acgacgaact gcgctgggac ggtgaactga ccgtcacacg ccatgatcgg      60
gagaccggta cgactttcgt gattcgaatc gactccaccc gtctgggacc ggcgtcgggt     120
ggcacgcggg ccgctcacta tccctcgatc ggccacgctc tggcggacgc cgggaagctc     180
gccggtgcaa tgactttgaa gatggctgtc tccgacctgc cgatgggtgg cgggaagtcg     240
gtgatcgcac tgccagcacc cgcaatcag atcgacgccg caacctggtc tcgtatcctc     300
ggcatccacg ccgagaacat cgacaagctc gaaggaaact actggaccgg tcccgacgtc     360
aacaccaact cttccgacat ggatcagctc agtcgcacca ccagatacgt cttcgggcgt     420
tcggttgaca agggtggcgc cggttccagc gcgcacgcca ccgctctggg tgtgttcgaa     480
gcgatgaagg ccacggcgcg tcgccgagga ctcggaacac tcgacggccg aacggtactg     540
gtacaggggc tcggcgccgt cggcggcgac gtcgtccgtc tcgcagcgca ggctggcgca     600
cgtctgctgg ttgccgatac ggacccgcag cgcctcgagg cggcttctct cgcggggcac     660
acggtcgttc ctgccggcga ggtcctccga acaccgtgtg acctctttgc ccctgcgcg     720
atgggaggca tcatcgattt cgctgcggct gcgtcgattc cgactctggc cgtggcgggc     780
gcagcaaaca acatcttgac cgatgccgct gccggtgagg ttctgcgaga ccgcggggtt     840
ctctgtgccc ctgatttcgt cgcgaacgca ggcggagcct ttcacctcgt ggggcgagaa     900
gtcctggggt ggaacgaaga ctacgtcgtc gaacgaaccc gcgggatcgg tcgaaccttg     960
gacgaggtgt actcgttgag cgaggaacgt ggcatcacta ccgaggccgc agcgcttatg    1020
ctcgcccggg cgcggctatc ccccgcatcc accgccgccg ccgccacatc cgccgccccc    1080
gctgcagctg ctgcctcccc cgcctga                                        1107
```

<210> SEQ ID NO 3
<211> LENGTH: 17
<212> TYPE: DNA
<213> ORGANISM: Artificial

```
<220> FEATURE:
<223> OTHER INFORMATION: Primer-1

<400> SEQUENCE: 3
atgathgayg aygaryt                                                  17

<210> SEQ ID NO 4
<211> LENGTH: 17
<212> TYPE: DNA
<213> ORGANISM: Artificial
<220> FEATURE:
<223> OTHER INFORMATION: Primer-2
<220> FEATURE:
<221> NAME/KEY: misc_feature
<222> LOCATION: (1)..(17)
<223> OTHER INFORMATION: n represents A, T, G or C.

<400> SEQUENCE: 4
ccngtccart arttncc                                                  17

<210> SEQ ID NO 5
<211> LENGTH: 20
<212> TYPE: DNA
<213> ORGANISM: Artificial
<220> FEATURE:
<223> OTHER INFORMATION: Primer-3

<400> SEQUENCE: 5
agatggctgt ctccgacctg                                               20

<210> SEQ ID NO 6
<211> LENGTH: 20
<212> TYPE: DNA
<213> ORGANISM: Artificial
<220> FEATURE:
<223> OTHER INFORMATION: Primer-4

<400> SEQUENCE: 6
cagacgggtg gagtcgattc                                               20

<210> SEQ ID NO 7
<211> LENGTH: 1329
<212> TYPE: DNA
<213> ORGANISM: Rhodococcus qingshengii

<400> SEQUENCE: 7
aagtggggcg tttcatccac gcgcacccca gtcagaacga agcgttgggc gaggccatgc    60
tcgcactcgc gggaacacca ctgcacgccc acaactgacc cggagacaga aaaggagatt   120
caatgagtat cgacgacgaa ctgcgctggg acggtgaact gaccgtcaca cgccatgatc   180
gggagaccgg tacgactttc gtgattcgaa tcgactccac ccgtctggga ccggcgtcgg   240
gtggcacgcg ggccgctcac tatccctcga tcggccacgc tctggcggac gccgggaagc   300
tcgccggtgc aatgactttg aagatggctg tctccgacct gccgatgggt ggcgggaagt   360
cggtgatcgc actgccagca ccgcgcaatc agatcgacgc cgcaacctgg tctcgtatcc   420
tcggcatcca cgccgagaac atcgacaagc tcgaaggaaa ctactggacc ggtcccgacg   480
tcaacaccaa ctcttccgac atggatcagc tcagtcgcac caccagatac gtcttcgggc   540
gttcggttga caagggtggc gccggttcca gcgcgcacgc caccgctctg ggtgtgttcg   600
aagcgatgaa ggccacggcg cgtcgccgag gactcggaac actcgacggc cgaacggtac   660
tggtacaggg gctcggcgcc gtcggcggcg acgtcgtccg tctcgcagcg caggctggcg   720
```

-continued

```
cacgtctgct ggttgccgat acggacccgc agcgcctcga ggcggcttct ctcgcggggc      780
acacggtcgt tcctgccggc gaggtcctcc gaacaccgtg tgacctcttt gcccctgcg      840 cgatgggagg catcatcgat ttcgctgcgg ctgcgtcgat tccgactctg gccgtggcgg     900
gcgcagcaaa caacatcttg accgatgccg ctgccggtga ggttctgcga gaccgcgggg    960
ttctctgtgc ccctgatttc gtcgcgaacg caggcggagc ctttcacctc gtggggcgag   1020
aagtcctggg gtggaacgaa gactacgtcg tcgaacgaac ccgcgggatc ggtcgaacct    1080
tggacgaggt gtactcgttg agcgaggaac gtggcatcac taccgaggcc gcagcgctta   1140
tgctcgcccg ggcgcggcta tcccccgcat ccaccgccgc cgccgccaca tccgccgccc    1200
ccgctgcagc tgctgcctcc cccgcctgaa ccgccaccgt ccgaacccccc gctacttccg   1260 ctgccgtcgg caccgattcc ggcggcggag gccaaggcgg gattgatcat cagcatcgcc   1320
gaaccggcg                                                            1329
```

```
<210> SEQ ID NO 8
<211> LENGTH: 43
<212> TYPE: DNA
<213> ORGANISM: Artificial
<220> FEATURE:
<223> OTHER INFORMATION: Primer-5

<400> SEQUENCE: 8
ccggaattct aaggaggtta acaatgagta tcgacgacga act                43

<210> SEQ ID NO 9
<211> LENGTH: 29
<212> TYPE: DNA
<213> ORGANISM: Artificial
<220> FEATURE:
<223> OTHER INFORMATION: Promer-6

<400> SEQUENCE: 9
cggggtacct caggcggggg aggcagcag                               29
```